United States Patent
Yoshida et al.

(10) Patent No.: US 10,501,811 B2
(45) Date of Patent: Dec. 10, 2019

(54) METHOD FOR SORTING TISSUE CELLS

(71) Applicant: KYOTO UNIVERSITY, Kyoto-shi, Kyoto (JP)

(72) Inventors: Yoshinori Yoshida, Kyoto (JP); Hirohide Saito, Kyoto (JP); Kenji Miki, Kyoto (JP); Kei Endo, Kyoto (JP); Seiya Takahashi, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 15/568,209

(22) PCT Filed: Apr. 22, 2016

(86) PCT No.: PCT/JP2016/062710
§ 371 (c)(1),
(2) Date: Dec. 1, 2017

(87) PCT Pub. No.: WO2016/171235
PCT Pub. Date: Oct. 27, 2016

(65) Prior Publication Data
US 2018/0100203 A1 Apr. 12, 2018

(30) Foreign Application Priority Data
Apr. 22, 2015 (JP) ................................ 2015-087805

(51) Int. Cl.
*C12Q 1/6888* (2018.01)
*C12Q 1/68* (2018.01)
*C12N 15/113* (2010.01)
*C12N 15/67* (2006.01)
*C12N 5/071* (2010.01)

(52) U.S. Cl.
CPC .......... *C12Q 1/6888* (2013.01); *C12N 5/067* (2013.01); *C12N 5/069* (2013.01); *C12N 5/0676* (2013.01); *C12N 15/113* (2013.01); *C12N 15/67* (2013.01); *C12Q 1/68* (2013.01); *C12N 2506/45* (2013.01); *C12Q 2600/178* (2013.01)

(58) Field of Classification Search
CPC .... C12N 5/0606; C12N 15/67; C12N 15/113; C12Q 2600/178
USPC .... 435/6.1, 91.1, 91.31, 325, 375, 455, 458; 536/23.1, 24.5
See application file for complete search history.

(56) References Cited

U.S. PATENT DOCUMENTS

| 9,057,065 B2 | 6/2015 | Inoue et al. |
| 2011/0196017 A1 | 8/2011 | Olson et al. |
| 2012/0128643 A1 | 5/2012 | Biffi et al. |
| 2014/0199688 A1 | 7/2014 | Mizuguchi et al. |

FOREIGN PATENT DOCUMENTS

| JP | 2012-500199 A | 1/2012 |
| JP | 2012-525141 A | 10/2012 |
| WO | WO 2009/066758 A1 | 5/2009 |
| WO | 2011/154553 | 12/2011 |
| WO | WO 2013/027427 A1 | 2/2013 |
| WO | WO 2014/113089 A2 | 7/2014 |

OTHER PUBLICATIONS

Lahmy et al, Mol. Biol. Rep., vol. 41, pp. 2055-2066 (Year: 2014).*
Poy et al, PNAS, vol. 106, No. 14, pp. 5813-5818 (Year: 2009).*
Poy et al (Nature, vol. 432, No. 11, pp. 226-230 (Year: 2004).*
Kajiwara et al. "Donor-dependent variations in hepatic differentiation from human-induced pluripotent stem cells", *PNAS* 109(31):12538-12543 (2012).
Kunisada et al, "Small molecules induce efficient differentiation into insulin-producing cells from human induced pluripotent stem cells", *Stem Cell Research* 8:274-284 (2012).
Lahmy et al. "miRNA-375 promotes beta pancreatic differentiation in human induced pluripotent stem (hiPS) cells", *Mol. Biol Rep* 41:2055-2066 (2014).
Nakagawa et al, "A novel efficient feeder-free culture system for the derivation of human induced pluripotent stem cells", *Scientific Reports* 4:3594 (2014) 7 pages.
Miki et al, "Efficient Detection and Purification of Cell Populations Using Synthetic MicroRNA Switches", *Cell Stem Cell* 16:699-711 (2015).
Miki et al. "Efficient detection and purification of cells by synthetic microRNA switches", *Regenerative Medicine* 14(Suppl 2015):188 (2015).
International Search Report corresponding to International Application No. PCT/JP2016/062710 dated Jun. 21, 2016.
Miki K, et al., "Supplemental Information: Efficient Detection and Purification of Cell Populations Using Synthetic MicroRNA Switches", published online May 21, 2015. Cell Stem Cell, Jun. 4, 2015 (Jun. 4, 2015), pp. 1-28.
Ozcan "Minireview: MicroRNA Function in Pancreatic Beta Cells", Mo. Endocrinol. 28(12):1922-1933 (2014).
Poy et al. "A pancreatic islet-specific microRNA regulates insulin secretion", Nature 432(7014):226-230 (2004).
Poy et al. "miR-375 maintains normal pancreatic alpha and beta cell mass", PNAS 106(14):5813-5818 (2009).
Tang et al. "Role of microRNAs in diabetes", Biochimica et Biophysica Acta 1779(11):697-701 (2008).

(Continued)

*Primary Examiner* — Jane J Zara
(74) *Attorney, Agent, or Firm* — Myers Bigel, P.A.

(57) ABSTRACT

An object of the present invention is to provide a method for increasing the purity of a type of tissue cell such as an endothelial cell, a hepatocyte, or an insulin-producing cell. The present invention solves the problem by providing a method comprising a step of introducing, into a cell population, an mRNA comprising a nucleic acid sequence recognized by an miRNA specifically expressed in endothelial cells, hepatocytes, or insulin-producing cells.

3 Claims, 7 Drawing Sheets

Specification includes a Sequence Listing.

(56) References Cited

OTHER PUBLICATIONS

Zhang et al. "miR-375 Inhibits Proliferation of Mouse Pancreatic Progenitor Cells by Targeting YAP1", Cell Physiol Biochem 32(6):1801-1817 (2013).
Partial Supplementary European Search Report corresponding to European Application No. 16783256.7 dated Dec. 7, 2018.

* cited by examiner four types of mRNA that included a tandem target miRNA sequence

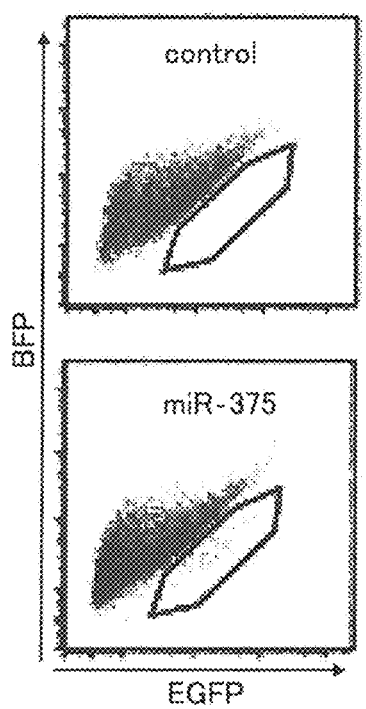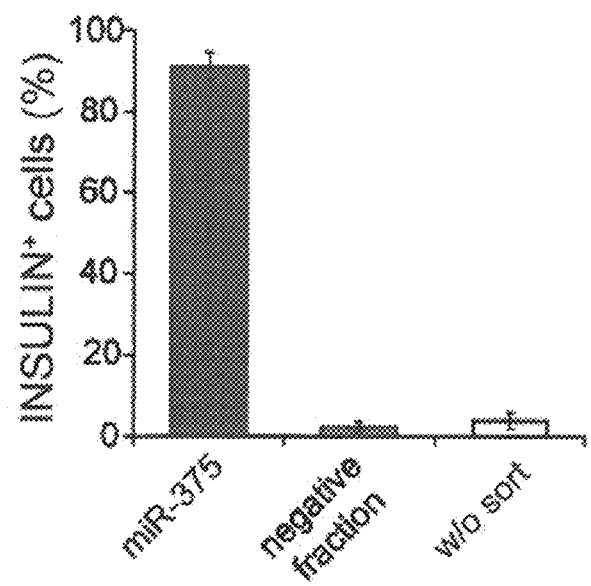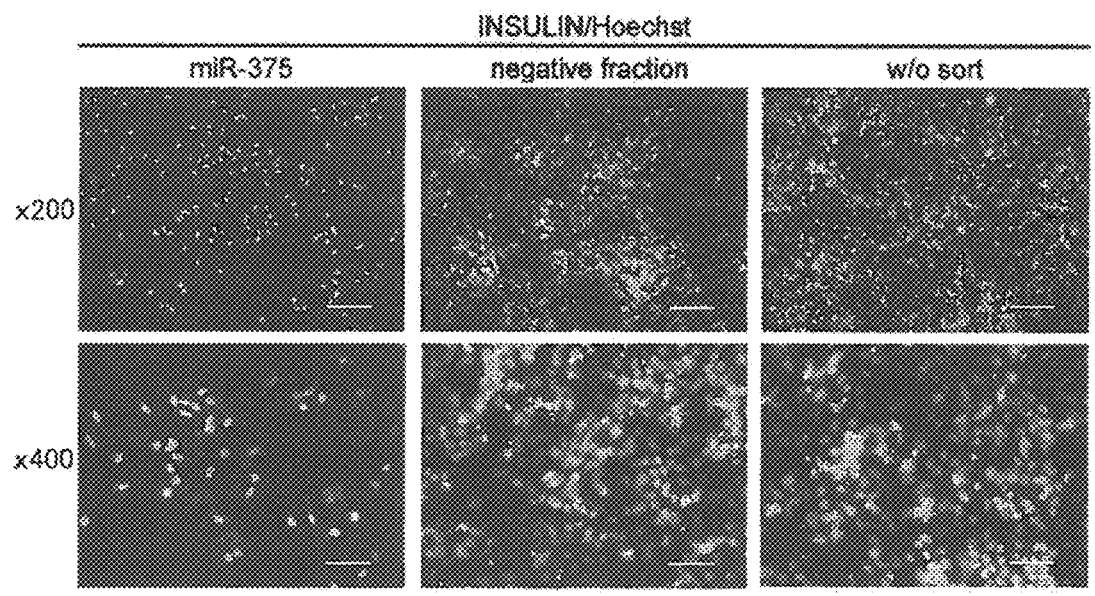

METHOD FOR SORTING TISSUE CELLS

RELATED APPLICATIONS

This application is a 35 U.S.C. § 371 national phase application of PCT Application PCT/JP2016/062710 filed Apr. 22, 2016, which claims priority to Japanese Application No. 2015-087805 filed Apr. 22, 2015. The entire contents of each are incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 5576-341_ST25.txt, 14,447 bytes in size, generated on Oct. 19, 2017 and filed via EFS-Web, is provided in lieu of a paper copy. This Sequence Listing is incorporated by reference into the specification for its disclosures.

TECHNICAL FIELD

The present invention relates to a method for sorting tissue cells, and in particular, relates to a method for sorting an endothelial cell, a hepatocyte, and an insulin-producing cell.

BACKGROUND ART

Much attention has been paid to cell transplantation therapy using pluripotent stem cells, and methods for inducing each tissue cell have been reported (Non-Patent Literatures 1, 2, and 3). However, all the cells induced are not just a desired type of cell and usually contain other types of cell at the same time. To use such a cell population as cells used for transplantation, it is necessary to increase the purity of a desired type of cell by sorting, etc.

Recently, a method has been conducted in which a desired type of cell is sorted by using one or more cell surface markers. Unfortunately, a specific surface marker has not been identified with respect to every tissue cell type.

CITATION LIST

Non Patent Literature

Non Patent Literature 1: Kajiwara M, et al., Proc Natl Acad Sci USA. 109:12538-12543, 2012
Non Patent Literature 2: Kunisada Y, et al., Stem Cell Res. 8:274-284, 2012
Non Patent Literature 3: Nakagawa, M, et al., Sci Rep 4, 3594, 2014

SUMMARY OF INVENTION

Problems to be Solved by the Invention

In view of the above conventional technique, a novel sorting method from another viewpoint is desirable so as to increase the purity of a target type of tissue cell. That is, an object of the present invention is to provide a tool for sorting each type of tissue cell.

Means for Solving the Problems

The present inventors have conducted intensive research to solve the above problem and then have found that each miRNA-responsive mRNA can be used to allow a type of tissue cell such as an endothelial cell, a hepatocyte, or an insulin-producing cell to be purified with high purity. Specifically, miRNAs expressed specifically in each tissue cell population were identified by microarray analysis. Then, an mRNA (miRNA switch) having a marker gene and a target sequence of each of the above miRNAs was constructed. Then, this mRNA was introduced into cells that were subject to sorting. In the cell population, cells exhibiting different behavior were found to be present. When sorted, these cells were confirmed to be a target type of tissue cell with high purity. In this way, a desired tissue cell sorting method was discovered. The present invention has been completed based on such findings.

Specifically, the present invention provides the following items.

[1] A method for sorting an endothelial cell, comprising introducing an miRNA-responsive mRNA into a cell population, the miRNA-responsive mRNA comprising:
  (i) a nucleic acid sequence recognized specifically by miR-126-3P or miR-126-5P; and
  (ii) a nucleic acid sequence corresponding to a coding region of a first marker gene.

[2] A method for sorting a hepatocyte, comprising introducing an miRNA-responsive mRNA into a cell population, the miRNA-responsive mRNA comprising:
  (i) a nucleic acid sequence recognized specifically by miR-122-5P; and
  (ii) a nucleic acid sequence corresponding to a coding region of a first marker gene.

[3] A method for sorting an insulin-producing cell, comprising introducing an miRNA-responsive mRNA into a cell population, the miRNA-responsive mRNA comprising:
  (i) a nucleic acid sequence recognized specifically by miR-375; and
  (ii) a nucleic acid sequence corresponding to a coding region of a first marker gene.

[4] The method according to any one of items [1] to [3], wherein the miRNA-responsive mRNA comprises a nucleic acid sequence having (i) and (ii) linked in a 5' to 3' direction.

[5] The method according to any one of items [1] to [4], wherein the first marker gene of (ii) is one or more genes selected from the group consisting of a fluorescent protein-encoding gene, an apoptosis-inducing gene, and a suicide gene.

[6] The method according to item [5], wherein the fluorescent protein-encoding gene is a blue fluorescent protein (BFP)-encoding gene.

[7] The method according to item [5], wherein the apoptosis-inducing gene is a Bim protein-encoding gene.

[8] The method according to any one of items [1] to [7], wherein a cell having a low level of translation of the first marker gene is sorted as the cell of interest.

[9] The method according to any one of items [1] to [8], further comprising introducing, into the cell population, an mRNA consisting of a sequence comprising a nucleic acid corresponding to a coding region of a second marker gene, wherein a cell in which the second marker gene is translated is sorted as the cell of interest, and wherein the second marker gene is a fluorescent protein-encoding gene different from the first marker gene, or a drug resistance gene.

[10] The method according to any one of items [1] to [9], wherein the cell population is a cell population that has been induced to differentiate from a pluripotent stem cell.

[11] A method for producing endothelial cells, comprising:

(a) producing, from a pluripotent stem cell, a cell population containing endothelial cells;
(b) introducing, into the cell population of the step (a), an miRNA-responsive mRNA consisting of sequences comprising (i) a nucleic acid recognized specifically by miR-126-3P or miR-126-5P and (ii) a nucleic acid corresponding to a coding region of a first marker gene; and
(c) sorting a cell having a low level of translation of the first marker gene of the step (b).

[12] A method for producing hepatocytes, comprising:
(a) producing, from a pluripotent stem cell, a cell population containing hepatocytes;
(b) introducing, into the cell population of the step (a), an miRNA-responsive mRNA consisting of sequences comprising (i) a nucleic acid recognized specifically by miR-122-5P and (ii) a nucleic acid corresponding to a coding region of a first marker gene; and
(c) sorting a cell having a low level of translation of the first marker gene of the step (b).

[13] A method for producing insulin-producing cells, comprising:
(a) producing, from a pluripotent stem cell, a cell population containing insulin-producing cells;
(b) introducing, into the cell population of the step (a), an miRNA-responsive mRNA consisting of sequences comprising (i) a nucleic acid recognized specifically by miR-375 and (ii) a nucleic acid corresponding to a coding region of a first marker gene; and
(c) sorting a cell having a low level of translation of the first marker gene of the step (b).

[14] The method according to any one of items [11] to [13], wherein the miRNA-responsive mRNA comprises a nucleic acid sequence having (i) and (ii) linked in a 5' to 3' direction.

[15] The method according to any one of items [11] to [14], wherein the first marker gene of (ii) is one or more genes selected from the group consisting of a fluorescent protein-encoding gene, an apoptosis-inducing gene, and a suicide gene.

[16] The method according to any one of items [11] to [15], further comprising: introducing, into the cell population, an mRNA consisting of a sequence comprising a nucleic acid corresponding to a coding region of a second marker gene, wherein a cell in which the second marker gene is translated is sorted as the cell of interest, and wherein the second marker gene is a fluorescent protein-encoding gene different from the first marker gene, or a drug resistance gene.

Advantageous Effects of Invention

In accordance with the method of the present invention, tissue cells such as endothelial cells, hepatocytes, and insulin-producing cells can be easily sorted and purified to high purity. The mRNA that has been introduced into a cell population using the method according to the present invention is only transiently present in cells. Therefore, this makes it possible to sort target cells safely without the mRNA being introduced into the genome. In addition, the present invention discloses a method in which living cells can be sorted, without fixation, on the basis of the level of expression of an intracellular active miRNA. Further, cells purified in accordance with the method of the present invention can be used for transplantation therapy.

BRIEF DESCRIPTION OF DRAWINGS

FIG. 2A also shows the results obtained by gating the cells in each gate above and by staining them with an anti-CD31 antibody. The term "negative fraction" means that the results obtained by gating the cells outside the above gate and by staining them with the anti-CD31 antibody.

FIG. 5A also shows the flow cytometry analysis results obtained by gating the cells in the gate of the left panel, by staining them with an anti-ALUBUMIN or anti-HNF4A antibody, and by performing flow cytometry analysis.

FIG. 6A shows the flow cytometry analysis results obtained after miR-375 miRNA switch together with EGFP was introduced into an insulin-producing cell population derived from induced differentiation of iPS cells. FIG. 6B is a graph showing the percentage of insulin-positive cells in: cells sorted, using miR-375 miRNA switch from an insulin-producing cell population derived from induced differentiation of iPS cells; cells (negative fraction) other than the cells sorted using the miR-375 miRNA switch; and an insulin-producing cell population (w/o sort) derived from induced differentiation of the iPS cells. FIG. 6C shows the immunostaining results obtained by staining, with an anti-insulin antibody, cells sorted using miR-375 miRNA switch from an insulin-producing cell population derived from induced differentiation of iPS cells; cells (negative fraction) other than the cells sorted using the miR-375 miRNA switch; and an insulin-producing cell population (w/o sort) derived from induced differentiation of the iPS cells.

MODE FOR CARRYING OUT THE INVENTION

Figure 1A:
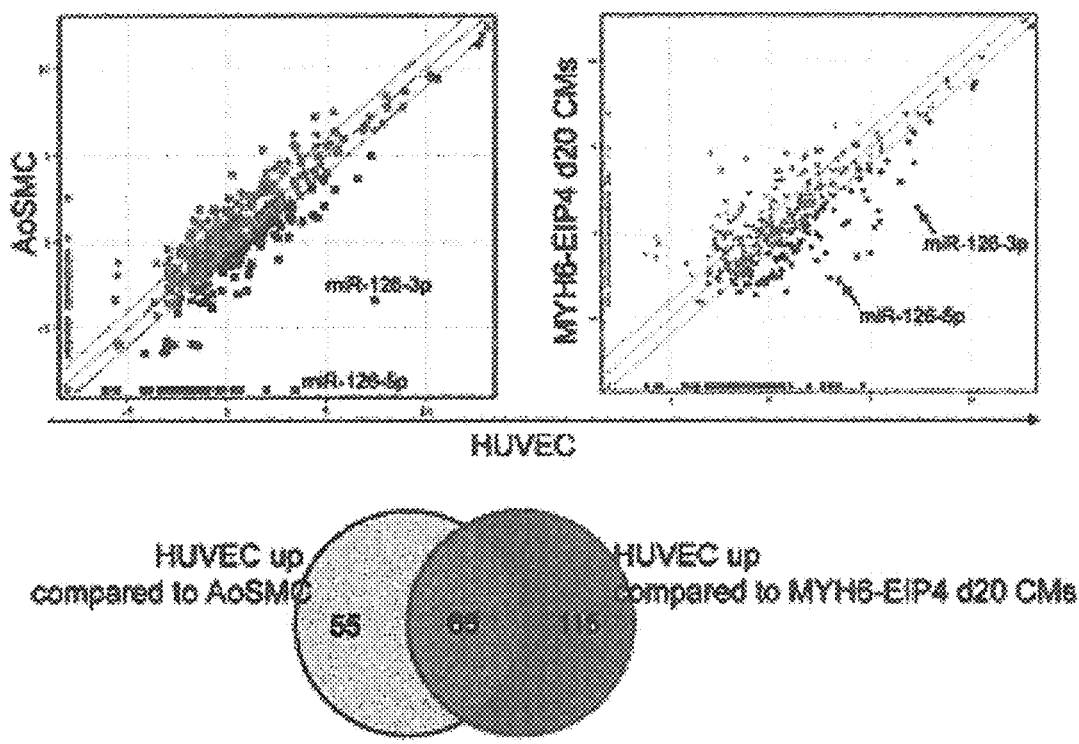
FIG. 1A shows the results of comparing, using a microarray, the levels of expression of miRNAs between HUVEC and smooth muscle cells (AoSMC) (left panel) or cardiomyocytes (MYH6-EIP4 d20 CMs) (right panel). The lower diagram is a Venn diagram showing the analysis results.

The following describes, in detail, embodiments of the present invention. The present invention, however, is not limited to the following Embodiments.

miRNA-Responsive mRNA

As used herein, the miRNA-responsive mRNA is also simply called an miRNA switch, and means an mRNA comprising the following nucleic acid sequences (i) and (ii): (i) a nucleic acid sequence specifically recognized by an miRNA; and (ii) a nucleic acid sequence corresponding to a coding region of a first marker gene. (i) The nucleic acid sequence specifically recognized by an miRNA and (ii) the nucleic acid sequence corresponding to a coding region of a first marker gene are operably linked.

As used herein, the "miRNA" refers to a non-coding RNA composed of a short chain (20 to 25 bases) that is present in a cell and is participated in the regulation of gene expression through mRNA degradation and/or inhibition of translation from an mRNA to a protein. This miRNA is first produced as a transcribed, single-stranded pri-miRNA, an miRNA of which, together with its complementary strand, can form a hairpin loop structure; a portion of the pri-miRNA is cleaved by an enzyme called Drosha present in the nucleus to give a pre-miRNA, which is exported outside the nucleus; and the pre-miRNA is further cleaved by Dicer to become functional.

The miRNA of (i) can be appropriately selected from an miRNA specifically expressed in a desired type of cell to be sorted. Examples of the desired type of cell include an endothelial cell, a hepatocyte, and an insulin-producing cell, as described below. The miRNA specifically expressed may be miRNAs, the expression levels of which are higher in a desired type of cell than in another type of cell by at least 10%, at least 20%, at least 30%, at least 40%, at least 50%, at least 60%, at least 70%, at least 80%, at least 90%, or more. Such an miRNA can be suitably selected from miRNAs registered on database information site (e.g., http://www.mirbase.org/ or http://www.microrna.org/) and/or miRNAs described in literature disclosed in the database. Examples include, but are not limited to, miRNAs listed in Table 1.

TABLE 1 miRNAs and the sequences thereof.
[Table 1]

| miRNA name | miRNA sequence (5' -> 3') | SEQ ID NO: |
|---|---|---|
| miR-126-3P | ucguaccgugaguaauaaugcg | 1 |
| miR-126-5P | cauuauuacuuuugguacgcg | 2 |
| miR-122-5P | uggagugugacaaugguguuug | 3 |
| miR-375 | uuuguucguucggcucgcguga | 4 |

In the present invention, the nucleic acid sequence specifically recognized by an miRNA is preferably a sequence perfectly complementary to the miRNA. Alternatively, the nucleic acid sequence may have a mismatch in the perfectly complementary sequence as long as the nucleic acid sequence can be recognized by the miRNA. The mismatch may be a mismatch that the miRNA can usually recognize. Regarding in vivo, intracellular, intrinsic functions, the degree of the mismatch may be about 40 to 50%. Examples of such a mismatch include, but are not particularly limited to, 1 base, 2 bases, 3 bases, 4 bases, 5 bases, 6 bases, 7 bases, 8 bases, 9 bases, and 10 bases; or 1% mismatch, 5% mismatch, 10% mismatch, 20% mismatch, 30% mismatch, and 40% mismatch per entire recognition sequence. In addition, like an miRNA target sequence included in a certain mRNA in a cell, many mismatches may be included in the 5' region of a target sequence, which region is outside a seed region and corresponds to about 16 bases located on the 3' side of the miRNA. The seed region may contain no mismatch or may contain mismatches: 1 base, 2 bases, or 3 bases. The length of such a sequence may be a base length corresponding to the number of bases that can bind specifically to RISC. The length of the sequence is preferably 18 bases or more and less than 24 bases and more preferably 20 bases or more and less than 22 bases. As used herein, a nucleic acid sequence specifically recognized by an miRNA may be used after determined by introducing an miRNA-responsive mRNA having the sequence into a desired type of cell and other cells; and by verifying that expression of a relevant marker gene is inhibited only in the desired type of cell. Examples of nucleic acid sequences specifically recognized by miR-126-3P, miR-126-5P, miR-122-5P, and miR-375 include, but are not limited to, target sequences listed in Table 2.

TABLE 2 miRNAs and the target sequences thereof.
[Table 2]

| miRNA name | miRNA target sequence (5' -> 3') | SEQ ID NO: |
|---|---|---|
| miR-126-3P | CGCATTATTACTCACGGTACGA | 5 |
| miR-126-5P | CGCGTACCAAAAGTAATAATG | 6 |
| miR-122-5P | CAAACACCATTGTCACACTCCA | 7 |
| miR-375 | TCACGCGAGCCGAACGAACAAA | 8 |

The (ii) "marker gene" used herein refers to a gene encoding any protein that functions as a marker after translation in a cell and enables cell sorting. Examples of a gene encoding the protein that functions as a marker after translation in a cell include, but are not limited to, genes encoding fluorescent proteins, light-emitting proteins, chromogenic proteins or fluorescence proteins; genes encoding proteins that help fluorescent proteins, etc., emit fluorescence, light, or color for visualization and quantification; and genes encoding proteins that kill cells when expressed (e.g., a membrane protein-encoding gene, an apoptosis-inducing gene, a suicide gene). In combination of an apoptosis-inducing gene, an apoptosis-inhibiting gene may be used as another marker gene. As used herein, a marker protein refers to a protein translated from an mRNA containing a nucleic acid corresponding to a coding region of the marker gene. As used herein, the term "first" is a term used to distinguish between two marker genes when used and is not restricted to a specific marker gene.

Examples of the fluorescent protein include, but are not limited to, blue fluorescent proteins (e.g., Sirius, BFP, EBFP); cyan fluorescent proteins (e.g., mTurquoise, TagCFP, AmCyan, mTFP1, MidoriishiCyan, CFP); green fluorescent proteins (e.g., TurboGFP, AcGFP, TagGFP, Azami-Green (e.g., hmAG1), ZsGreen, EmGFP, EGFP, GFP2, HyPer); yellow fluorescent proteins (e.g., TagYFP, EYFP, Venus, YFP, PhiYFP, PhiYFP-m, TurboYFP, ZsYellow, mBanana); orange fluorescent proteins (e.g., KusabiraOrange (e.g., hmK02), mOrange); red fluorescent proteins (e.g., TurboRFP, DsRed-Express, DsRed2, TagRFP, DsRed-Monomer, AsRed2, mStrawberry); and near-infrared fluorescent proteins (e.g., TurboFP602, mRFP1, JRed, KillerRed, mCherry, HcRed, KeimaRed (e.g., hdKeimaRed), mRasberry, mPlum).

As used herein, examples of the light-emitting protein include, but are not limited to, Aequorin. In addition, examples of the protein that helps emit fluorescence, light, or color include, but are not limited to, enzymes that degrade fluorescent, light-emitting, or chromogenic precursors (e.g., luciferase, phosphatase, peroxidase, β-lactamase). As used herein, when a substance that helps emit fluorescence, light, or color is used as a substance encoded by a marker gene, a relevant precursor is made to contact a cell population or the relevant precursor is introduced into the cell population during target cell sorting.

As used herein, the apoptosis-inducing gene means a gene encoding a protein having activity of inducing cellular apoptosis. Examples include, but are not limited to, IκB, Smac/DIABLO, ICE, HtrA2/OMI, AIF, endonuclease G, Bax, Bak, Noxa, Hrk (harakiri), Mtd, Bim, Bad, Bid, PUMA, activated caspase-3, Fas, and Tk. In the present invention, Bim is preferably used as the apoptosis-inducing gene.

As used herein, a suicide gene is a gene, the cellular expression of which is lethal to the cell. As used herein, the suicide gene product (e.g., diphtheria toxin A), by itself, may cause cell death. In addition, expression of such a gene may make cells susceptible to a specific chemical (e.g., expression of herpes simplex virus thymidine kinase gene can make cells susceptible to an anti-virus compound). Examples of the suicide gene include, but are not limited to, genes encoding: diphtheria toxin A; herpes simplex virus thymidine kinase (HSV-TK); carboxypeptidase G2 (CPG2); carboxyl esterase (CA); cytosine deaminase (CD); cytochrome P450 (cyt-450); deoxycytidine kinase (dCK); nitroreductase (NR); purine-nucleoside phosphorylase (PNP); thymidine phosphorylase (TP); varicella-zoster virus thymidine kinase (VZV-TK); and xanthine-guanine phosphoribosyl transferase (XGPRT). In the present invention, the HSV-TK gene is preferably used as the suicide gene.

As used herein, the marker gene may include a gene encoding a localization signal. Examples of the localization signal include a nuclear localization signal, a plasma membrane localization signal, a mitochondrial localization signal, and a protein secretion signal. Specific examples include, but are not limited to, a classical nuclear localization signal (NLS), M9 sequence, a mitochondrial target sequence (MTS), and an ER localization sequence. Such localization signals provide a particular advantage when imaging is used to carry out a step of sorting a target cell by, for example, imaging cytometry described below.

As used herein, the phrase "a nucleic acid sequence specifically recognized by an miRNA is operably linked to a nucleic acid sequence corresponding to a coding region of a first marker gene" means that at least one miRNA target sequence is included in a 5' UTR, a 3' UTR of an open reading frame (including a start codon) encoding a marker gene and/or the open reading frame. An miRNA-responsive mRNA includes, preferably from the 5' end, in the 5' to 3' direction, a cap structure (7-methylguanosine 5'-phosphate), and an open reading frame encoding a marker gene, and a poly-A tail, and also includes at least one miRNA target sequence in a 5' UTR, a 3' UTR, and/or the open reading frame. The position of the miRNA target sequence of the mRNA may be located at the 5' UTR or 3' UTR or located within the open reading frame (on the 3' side of the start codon), all of which may each be provided with an miRNA target sequence. Hence, the number of the miRNA target sequences may be 1, 2, 3, 4, 5, 6, 7, 8, or more.

Preferably, the nucleic acid sequences (i) and (ii) of the miRNA-responsive mRNA are linked from the 5' to 3' direction in this order. At this time, the number and kinds of bases between the cap structure and the miRNA target sequence may be freely chosen as long as the bases involve neither a stem structure nor a specific conformation. For instance, in some designs, the number of bases between the cap structure and the miRNA target sequence is from 0 to 50 and preferably from 10 to 30. In addition, the number and kinds of bases between the miRNA target sequence and the start codon may be freely chosen as long as the bases involve neither a stem structure nor a specific conformation. For instance, in some designs, the number of bases between the miRNA target sequence and the start codon is from 0 to 50 and preferably from 10 to 30.

In the present invention, the miRNA target sequence of an miRNA-responsive mRNA preferably includes no AUG, a start codon. For example, when an miRNA target sequence is present in a 5' UTR and the target sequence contains AUG, it is preferable to design such that the AUG is in the same frame of a marker gene linked on the 3' side. Alternatively, when the target sequence contains AUG, the AUG in the target sequence may be changed to GUG. Further, to minimize the effect of AUG in the target sequence, the position of the target sequence in the 5' UTR may be changed appropriately. For instance, in some position designs, the number of bases between the cap structure and the AUG sequence in the target sequence is from 0 to 60 such as from 0 to 15, from 10 to 20, from 20 to 30, from 30 to 40, from 40 to 50, and from 50 to 60.

When an miRNA target sequence is present in a 5' UTR in the present invention, the following sequences, for example, may be used.

Table 3. miRNAs and the 5' UTR sequences of corresponding miRNA-responsive mRNAs.

TABLE 3

| miRNA name | 5' UTR sequence (5' -> 3') in miRNA-responsive mRNA (AUG at the 3' end indicates a start codon) | SEQ ID NO: |
|---|---|---|
| miR-126-3P | GGUUCCUUAAUCGCGGAUCCCGCAUUAUUACUCACGGUACGAAGAUCACACCGGUCGCCACCAUG | 9 |
| miR-126-5P | GGUUCCUUAAUCGCGGAUCCCGCGUACCAAAAGUAAUAAUGAGAUCACACCGGUCGCCACCAUG | 10 |
| miR-122-5P | GGUUCCUUAAUCGCGGAUCCCAAACACCAUUGUCACACUCCAAGAUCACACCGGUCGCCACCAUG | 11 |
| miR-375 | GGUUCCUUAAUCGCGGAUCCUCACGCGAGCCGAACGAACAAAAGAUCACACCGGUCGCCACCAUG | 12 |

When an miRNA target sequence is present in a 5' UTR in the present invention, the following sequence, for example, may be used downstream (i.e., in a 3' UTR) of a subsequent marker gene. At this time, any one of the above-described genes may be used as the marker gene interposed between the 5' UTR and the 3' UTR.

TABLE 4

| 3' UTR sequence | SEQ ID NO: |
|---|---|
| CCUGUGAUGCAGAAGAAAACACUCGGCUGGGAGGCCUUCACCGAGACGCUGUACCCCGCUGACGGCGGCCUG | 13 |

TABLE 4-continued

| 3' UTR sequence | SEQ ID NO: |
|---|---|
| GAAGGCAGAAACGACAUGGCCCUGAAGCUCGUGGGCGGGAGCCAUCUGAUCGCAAACAUCAAGACCACAUAUAGAUCCAAGAAACCCGCUAAGAACCUCAAGAUGCCUGGCGUCUACUAUGUGGACUACAGACUGGAAAGAAUCAAGGAGGCCAACAACGAGACCUACGUCGAGCAGCACGAGGUGGCAGUGGCCAGAUACUGCGACCUCCCUAGCAAACUGGGGCACAGAUCUCAUAUGCAUCUCGAGUGAUAGUCUAGACCUUCUGCGGGGCUUGCCUUCUGGCCAUGCCCUUCUUCUCUCCCUUGCACCUGUACCUCUUGGUCUUUGAAUAAAGCCUGAGUAGGAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAA | |

When a gene encoding BFP, for example, is used as a marker gene in the present invention, the following sequences may each be employed as a full-length miRNA-responsive mRNA according to the present invention.

TABLE 5 miRNAs and the full-length sequences of corresponding miRNA-responsive mRNAs.

| Name of miRNA-responsive mRNA | Full-length miRNA-responsive mRNA | SEQ ID NO: |
|---|---|---|

[Table 5-1]

| miR-126-3P | GGUUCCUUAAUCGCGGAUCCCGCAUUAUUACUCACGGUACGAAGAUCACACCGGUCGCCACCAUGGGAUCCAGCGAGCUGAUUAAGGAGAACAUGCACAUGAAGCUGUACAUGGAGGGCACCGUGGACAACCAUCACUUCAAGUGCACAUCCGAGGGCGAAGGCAAGCCCUACGAGGGCACCCAGACCAUGAGAAUCAAGGUGGUCGAGGGCGGCCCUCUCCCCUUCGCCUUCGACAUCCUGGCUACUAGCUUCCUCUACGGCAGCAAGACCUUCAUCAACCACACCCAGGGCAUCCCCGACUUCUUCAAGCAGUCCUUCCCUGAGGGCUUCACAUGGGAGAGAGUCACCACAUACGAAGACGGGGGCGUGCUGACCGCUACCCAGGACACCAGCCUCCAGGACGGCUGCCUCAUCUACAACGUCAAGAUCAGAGGGGUGAACUUCACAUCCAACGGCCCUGUGAUGCAGAAGAAAACACUCGGCUGGGAGGCCUUCACCGAGACGCUGUACCCCGCUGACGGCGGCCUGGAAGGCAGAAACGACAUGGCCCUGAAGCUCGUGGGCGGGAGCCAUCUGAUCGCAAACAUCAAGACCACAUAUAGAUCCAAGAAACCCGCUAAGAACCUCAAGAUGCCUGGCGUCUACUAUGUGGACUACAGACUGGAAAGAAUCAAGGAGGCCAACAACGAGACCUACGUCGAGCAGCACGAGGUGGCAGUGGCCAGAUACUGCGACCUCCCUAGCAAACUGGGGCACAGAUCUCAUAUGCAUCUCGAGUGAUAGUCUAGACCUUCUGCGGGGCUUGCCUUCUGGCCAUGCCCUUCUUCUCUCCCUUGCACCUGUACCUCUUGGUCUUUGAAUAAAGCCUGAGUAGGAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAA | 14 |

TABLE 5-continued miRNAs and the full-length sequences of corresponding miRNA-responsive mRNAs.

| Name of miRNA-responsive mRNA | Full-length miRNA-responsive mRNA | SEQ ID NO: |
|---|---|---|
| miR-126-5P | GGUUCCUUAAUCGCGGAUCCCGCGUACCAAAAGUAAUAAUG AGAUCACACCGGUCGCCACCAUGGGAUCCAGCGAGCUGAUU AAGGAGAACAUGCACAUGAAGCUGUACAUGGAGGGCACCGU GGACAACCAUCACUUCAAGUGCACAUCCGAGGGCGAAGGCA AGCCCUACGAGGGCACCCAGACCAUGAGAAUCAAGGUGGUC GAGGGCGGCCCUCUCCCCUUCGCCUUCGACAUCCUGGCUAC UAGCUUCCUCUACGGCAGCAAGACCUUCAUCAACCACACCC AGGGCAUCCCCGACUUCUUCAAGCAGUCCUUCCCUGAGGGC UUCACAUGGGAGAGAGUCACCACAUACGAAGACGGGGGCGU GCUGACCGCUACCCAGGACACCAGCCUCCAGGACGGCUGCC UCAUCUACAACGUCAAGAUCAGAGGGGUGAACUUCACAUCC AACGGCCCUGUGAUGCAGAAGAAAACACUCGGCUGGGAGGC CUUCACCGAGACGCUGUACCCCGCUGACGGCGGCCUGGAAG GCAGAAACGACAUGGCCCUGAAGCUCGUGGGCGGGAGCCAU CUGAUCGCAAACAUCAAGACCACAUAUAGAUCCAAGAAACCC GCUAAGAACCUCAAGAUGCCUGGCGUCUACUAUGUGGACUA CAGACUGGAAAGAAUCAAGGAGGCCAACAACGAGACCUACG UCGAGCAGCACGAGGUGGCAGUGGCCAGAUACUGCGACCUC CCUAGCAAACUGGGGCACAGAUCUCAUAUGCAUCUCGAGUG AUAGUCUAGACCUUCUGCGGGGCUUGCCUUCUGGCCAUGC CCUUCUUCUCUCCCUUGCACCUGUACCUCUUGGUCUUUGAA UAAAGCCUGAGUAGGAAAAAAAAAAAAAAAAAAAAAAAAA AAAAAAAAAAAAAAAAAAAAAAAAAAAAAAAAAAAAAAA AAAAAAAAAAAAAAAAAAAAAAAAAAAAAAAAAAAAAAA AAAAAAA | 15 |

[Table 5-2]

| miR-122-5P | GGUUCCUUAAUCGCGGAUCCCAAACACCAUUGUCACACUCC AAGAUCACACCGGUCGCCACCAUGGGAUCCAGCGAGCUGAU UAAGGAGAACAUGCACAUGAAGCUGUACAUGGAGGGCACCG UGGACAACCAUCACUUCAAGUGCACAUCCGAGGGCGAAGGC AAGCCCUACGAGGGCACCCAGACCAUGAGAAUCAAGGUGGU CGAGGGCGGCCCUCUCCCCUUCGCCUUCGACAUCCUGGCUA CUAGCUUCCUCUACGGCAGCAAGACCUUCAUCAACCACACC CAGGGCAUCCCCGACUUCUUCAAGCAGUCCUUCCCUGAGGG CUUCACAUGGGAGAGAGUCACCACAUACGAAGACGGGGGCG UGCUGACCGCUACCCAGGACACCAGCCUCCAGGACGGCUGC CUCAUCUACAACGUCAAGAUCAGAGGGGUGAACUUCACAUC CAACGGCCCUGUGAUGCAGAAGAAAACACUCGGCUGGGAGG CCUUCACCGAGACGCUGUACCCCGCUGACGGCGGCCUGGAA GGCAGAAACGACAUGGCCCUGAAGCUCGUGGGCGGGAGCCA UCUGAUCGCAAACAUCAAGACCACAUAUAGAUCCAAGAAACC CGCUAAGAACCUCAAGAUGCCUGGCGUCUACUAUGUGGACU ACAGACUGGAAAGAAUCAAGGAGGCCAACAACGAGACCUAC GUCGAGCAGCACGAGGUGGCAGUGGCCAGAUACUGCGACCU CCCUAGCAAACUGGGGCACAGAUCUCAUAUGCAUCUCGAGU GAUAGUCUAGACCUUCUGCGGGGCUUGCCUUCUGGCCAUG CCCUUCUUCUCUCCCUUGCACCUGUACCUCUUGGUCUUUGA AUAAAGCCUGAGUAGGAAAAAAAAAAAAAAAAAAAAAAAA AAAAAAAAAAAAAAAAAAAAAAAAAAAAAAAAAAAAAAA AAAAAAAAAAAAAAAAAAAAAAAAAAAAAAAAAAAAAAA AAAAAAAA | 16 |
| miR-375 | GGUUCCUUAAUCGCGGAUCCUCACGCGAGCCGAACGAACAA AAGAUCACACCGGUCGCCACCAUGGGAUCCAGCGAGCUGAU UAAGGAGAACAUGCACAUGAAGCUGUACAUGGAGGGCACCG UGGACAACCAUCACUUCAAGUGCACAUCCGAGGGCGAAGGC AAGCCCUACGAGGGCACCCAGACCAUGAGAAUCAAGGUGGU CGAGGGCGGCCCUCUCCCCUUCGCCUUCGACAUCCUGGCUA CUAGCUUCCUCUACGGCAGCAAGACCUUCAUCAACCACACC CAGGGCAUCCCCGACUUCUUCAAGCAGUCCUUCCCUGAGGG CUUCACAUGGGAGAGAGUCACCACAUACGAAGACGGGGGCG UGCUGACCGCUACCCAGGACACCAGCCUCCAGGACGGCUGC CUCAUCUACAACGUCAAGAUCAGAGGGGUGAACUUCACAUC CAACGGCCCUGUGAUGCAGAAGAAAACACUCGGCUGGGAGG CCUUCACCGAGACGCUGUACCCCGCUGACGGCGGCCUGGAA GGCAGAAACGACAUGGCCCUGAAGCUCGUGGGCGGGAGCCA UCUGAUCGCAAACAUCAAGACCACAUAUAGAUCCAAGAAACC CGCUAAGAACCUCAAGAUGCCUGGCGUCUACUAUGUGGACU ACAGACUGGAAAGAAUCAAGGAGGCCAACAACGAGACCUAC GUCGAGCAGCACGAGGUGGCAGUGGCCAGAUACUGCGACCU CCCUAGCAAACUGGGGCACAGAUCUCAUAUGCAUCUCGAGU | 17 |

TABLE 5-continued miRNAs and the full-length sequences of corresponding miRNA-responsive mRNAs.

| Name of miRNA-responsive mRNA | Full-length miRNA-responsive mRNA | SEQ ID NO: |
|---|---|---|
| | GAUAGUCUAGACCUUCUGCGGGGCUUGCCUUCUGGCCAUG CCCUUCUUCUCUCCCUUGCACCUGUACCUCUUGGUCUUUGA AUAAAGCCUGAGUAGGAAAAAAAAAAAAAAAAAAAAAAAAA AAAAAAAAAAAAAAAAAAAAAAAAAAAAAAAAAAAAAAAA AAAAAAAAAAAAAAAAAAAAAAAAAAAAAAAAAAAAAAAA AAAAAAAA | |

Introduction of miRNA-Responsive mRNA

According to an embodiment of the present invention, an miRNA-responsive mRNA can be introduced as a form of DNA or mRNA.

When the miRNA-responsive mRNA is introduced as a form of DNA, examples of a technique used to introduce the DNA into a somatic cell include use of vectors (e.g., a virus, a plasmid, an artificial chromosome), lipofection, liposome, and microinjection. Examples of the virus vector include a retrovirus vector, a lentivirus vector (e.g., Cell, 126, pp. 663-676, 2006; Cell, 131, pp. 861-872, 2007; Science, 318, pp. 1917-1920, 2007), an adenovirus vector (Science, 322, 945-949, 2008), an adeno-associated virus vector, and a sendaivirus vector (WO 2010/008054). Examples of the artificial chromosome vector include a human artificial chromosome (HAC), a yeast artificial chromosome (YAC), and a bacterial artificial chromosome (BAC, PAC). As the plasmid, plasmids for mammalian cells may be used (Science, 322:949-953, 2008). In order to be able to express an miRNA-responsive mRNA, the vector may contain control sequences such as a promoter, an enhancer, a ribosome binding sequence, a terminator, and a polyadenylation site. Also, the vector, if needed, may further contain: a drug resistance gene (e.g., a kanamycin resistant gene, an ampicillin resistance gene, a puromycin resistance gene); a selection marker sequence (e.g., a thymidine kinase gene, a diphtheria toxin gene); and/or a reporter gene sequence (e.g., genes encoding green fluorescent protein (GFP), β-glucuronidase (GUS), FLAG).

When the miRNA-responsive mRNA is the form of RNA, examples of a technique for introducing the mRNA into a somatic cell include lipofection and microinjection. To suppress degradation, 5-methylcytidine and/or pseudouridine (TriLink Biotechnologies) may be incorporated into the RNA to be used (Warren L, (2010) Cell Stem Cell. 7: 618-630). Regarding the positions of modified bases, all or some of uridines or cytidines may be replaced by the modified base independently. When some of them are replaced, the percentage of the modified base may be freely chosen and the position or positions may be at random.

Two or more different miRNA-responsive mRNAs may be introduced. Alternatively, an miRNA-responsive mRNA and an mRNA as a control (hereinafter, sometimes referred to as a control mRNA) as described below may be introduced. In such cases, multiple mRNAs are preferably co-introduced. The ratio between two or more co-introduced mRNAs can be maintained in individual cells. So, the activity ratio between proteins expressed using these mRNAs can be also maintained in a corresponding cell population. At this time, the amount of each mRNA introduced varies depending on a cell population into which the mRNAs are introduced, the mRNAs introduced, and a method and reagent for the introduction, and may be suitably selected by those skilled in the art so as to achieve a desired level of translation thereof.

According to an embodiment of the present invention, a control mRNA, for example, consists of a sequence comprising a nucleic acid corresponding to a coding region of a marker gene or a sequence comprising a nucleic acid corresponding to a coding region of a drug resistance gene, and does not have an miRNA target site. According to a preferable embodiment, the control mRNA together with an miRNA-responsive mRNA is introduced into a cell population. Then, the control mRNA can function as a control for identifying and distinguishing a cell containing the miRNA-responsive mRNA from others. In addition, the control mRNA can also function as a control used when a level of signal (e.g., fluorescence and light) from the miRNA-responsive mRNA is quantified. The amount of the control mRNA introduced may be suitably selected by those skilled in the art so as to achieve a desired level of translation thereof.

Regarding the "drug resistance gene" as used herein, it is possible to use any gene that can express a protein resistant to a corresponding drug. Examples include, but are not limited to, antibiotic resistance genes. Examples of the antibiotic resistance gene include a kanamycin resistance gene, an ampicillin resistance gene, a puromycin resistance gene, a blasticidin resistance gene, a gentamicin resistance gene, a kanamycin resistance gene, a tetracycline resistance gene, and a chloramphenicol resistance gene. According to the present invention, a puromycin resistance gene or a blasticidin resistance gene is preferably used as the antibiotic resistance gene.

A sorting method according to an embodiment of the present invention more preferably includes a step of simultaneously introducing an miRNA-responsive mRNA and a control mRNA into a cell population containing a target cell. The step may be preferably performed by co-transfecting the miRNA-responsive mRNA and the control mRNA. Use of the control mRNA allows for sorting of, as a target cell, a cell in which a marker protein is less or hardly translated from the miRNA-responsive mRNA even if the efficiency of introducing the miRNA-responsive mRNA into cells is low.

According to the present invention, when a control mRNA is used, a marker gene included in the control mRNA is preferably different from a marker gene included in an miRNA-responsive mRNA. For instance, when the marker gene included in an miRNA-responsive mRNA is an apoptosis-inducing gene or a suicide gene, the marker gene included in the control mRNA may be a fluorescent protein-encoding gene. In this case, fluorescent cells are subjected to, for example, FACS sorting for selective separation. Then, cells with reduced levels of expression of the apoptosis-inducing gene or the suicide gene are sorted as target cells. This can improve sorting precision.

In addition, a control mRNA consisting of a sequence comprising a nucleic acid corresponding to a coding region of a drug resistance gene can be used with an miRNA-responsive mRNA consisting of a sequence comprising a nucleic acid corresponding to a coding region of any marker gene. In this case, cells containing the miRNA-responsive mRNA are resistant to the drug regardless of the kind of the marker gene, which can improve sorting precision.

In contrast, the same type of gene may be used for marker genes included in an miRNA-responsive mRNA and a control mRNA. For instance, fluorescent protein-encoding genes may be used for the marker genes included in an miRNA-responsive mRNA and a control mRNA. In this case, two corresponding fluorescent proteins should have different fluorescence wavelengths.

Note that the fluorescent protein-encoding gene may be replaced by a gene encoding a light-emitting protein or a protein that helps emit fluorescence, light, or color, which gene is likewise used in combination.

Examples of a control mRNA that can be used according to the present invention include, but are not particularly limited to, the following mRNAs.

TABLE 6

Control mRNAs

| Control mRNA | Sequence | SEQ ID NO: |
|---|---|---|
| [Table 6-1] | | |
| mRNA_tagBFP | GGGCGAAUUAAGAGAGAAAAGAAGAGUAAGAAGAAAUAUAA GACACCGGUCGCCACCAUGGGAUCCAGCGAGCUGAUUAAGG AGAACAUGCACAUGAAGCUGUACAUGGAGGGCACCGUGGAC AACCAUCACUUCAAGUGCACAUCCGAGGGCGAAGGCAAGCC CUACGAGGGCACCCAGACCAUGAGAAUCAAGGUGGUCGAGG GCGGCCCUCUCCCCUUCGCCUUCGACAUCCUGGCUACUAGC UUCCUCUACGGCAGCAAGACCUUCAUCAACCACACCCAGGG CAUCCCCGACUUCUUCAAGCAGUCCUUCCCUGAGGGCUUCA CAUGGGAGAGAGUCACCACAUACGAAGACGGGGGCGUGCUG ACCGCUACCCAGGACACCAGCCUCCAGGACGGCUGCCUCAU CUACAACGUCAAGAUCAGAGGGGUGAACUUCACAUCCAACG GCCCUGUGAUGCAGAAGAAAACACUCGGCUGGGAGGCCUUC ACCGAGACGCUGUACCCCGCUGACGGCGGCCUGGAAGGCAG AAACGACAUGGCCCUGAAGCUCGUGGGCGGGAGCCAUCUGA UCGCAAACAUCAAGACCACAUAUAGAUCCAAGAAACCCGCUA AGAACCUCAAGAUGCCUGGCGUCUACUAUGUGGACUACAGA CUGGAAAGAAUCAAGGAGGCCAACAACGAGACCUACGUCGA GCAGCACGAGGUGGCAGUGGCCAGAUACUGCGACCUCCCUA GCAAACUGGGGCACAGAUCUCAUAUGCAUCUCGAGUGAUAG UCUAGACCUUCUGCGGGGCUUGCCUUCUGGCCAUGCCCUU CUUCUCUCCCUUGCACCUGUACCUCUUGGUCUUUGAAUAAA GCCUGAGUAGGAAAAAAAAAAAAAAAAAAAAAAAAAAAAAA AAAAAAAAAAAAAAAAAAAAAAAAAAAAAAAAAAAAAAAA AAAAAAAAAAAAAAAAAAAAAAAAAAAAAAAAAAAAAAAA AAA | 18 |
| mRNA_EGFP | GGGCGAAUUAAGAGAGAAAAGAAGAGUAAGAAGAAAUAUAA GACACCGGUCGCCACCAUGGGAUCCGUGAGCAAGGGCGAGG AGCUGUUCACCGGGGUGGUGCCCAUCCUGGUCGAGCUGGA CGGCGACGUAAACGGCCACAAGUUCAGCGUGUCCGGCGAGG GCGAGGGCGAUGCCACCUACGGCAAGCUGACCCUGAAGUUC AUCUGCACCACCGGCAAGCUGCCCGUGCCCUGGCCCACCCU CGUGACCACCCUGACCUACGGCGuGCAGuGCUUCAGCCGCU ACCCCGACCACAUGAAGCAGCACGACUUCUUCAAGUCCGCC AUGCCCGAAGGCUACGUCCAGGAGCGCACCAUCUUCUUCAA GGACGACGGCAACUACAAGACCCGCGCCGAGGUGAAGUUCG AGGGCGACACCCUGGUGAACCGCAUCGAGCUGAAGGGCAUC GACUUCAAGGAGGACGGCAACAUCCUGGGGCACAAGCUGGA GUACAACUACAACAGCCACAACGUCUAUAUCAUGGCCGACA AGCAGAAGAACGGCAUCAAGGUGAACUUCAAGAUCCGCCAC AACAUCGAGGACGGCAGCGUGCAGCUCGCCGACCACUACCA GCAGAACACCCCCAUCGGCGACGGCCCCGUGCUGCUGCCCG ACAACCACUACCUGAGCACCCAGUCCGCCCUGAGCAAAGACC CCAACGAGAAGCGCGAUCACAUGGUCCUGCUGGAGUUCGUG ACCGCCGCCGGGAUCACUCUCGGCAUGGACGAGCUGUACAA GAGAUCUCAUAUGCAUCUCGAGUGAUAGUCUAGACCUUCUG CGGGGCUUGCCUUCUGGCCAUGCCCUUCUUCUCUCCCUUG CACCUGUACCUCUUGGUCUUUGAAUAAAGCCUGAGUAGGAA AAAAAAAAAAAAAAAAAAAAAAAAAAAAAAAAAAAAAAAA AAAAAAAAAAAAAAAAAAAAAAAAAAAAAAAAAAAAAAAA AAAAAAAAAAAAAAAAAAAAAAAAAAAA | 19 |

TABLE 6-continued

Control mRNAs

[Table 6-2]

| Control mRNA | Sequence | SEQ ID NO: |
|---|---|---|
| mRNA_Blastcidin | GGGCGAAUUAAGAGAGAAAAGAAGAGUAAGAAGAAAUAUAA GACACCGGUCGCCACCAUGGCCAAGCCUUUGUCUCAAGAAG AAUCCACCCUCAUUGAAAGAGCAACGGCUACAAUCAACAGCA UCCCCAUCUCUGAAGACUACAGCGUCGCCAGCGCAGCUCUC UCUAGCGACGGCCGCAUCUUCACUGGUGUCAAUGUAUAUCA UUUUACUGGGGGACCUUGUGCAGAACUCGUGGUGCUGGGC ACUGCUGCUGCUGCGGCAGCUGGCAACCUGACUUGUAUCG UCGCGAUCGGAAAUGAGAACAGGGGCAUCUUGAGCCCCUGC GGACGGUGCCGACAGGUGCUUCUCGAUCUGCAUCCUGGGA UCAAAGCCAUAGUGAAGGACAGUGAUGGACAGCCGACGGCA GUUGGGAUUCGUGAAUUGCUGCCCUCUGGUUAUGUGUGGG AGGGCUAAUCUAGACCUUCUGCGGGCUUGCCUUCUGGCC AUGCCCUUCUUCUCUCCCUUGCACCUGUACCUCUUGGUCUU UGAAUAAAGCCUGAGUAGGAAAAAAAAAAAAAAAAAAAAAAA AAAAAAAAAAAAAAAAAAAAAAAAAAAAAAAAAAAAAAAAAA AAAAAAAAAAAAAAAAAAAAAAAAAAAAAAAAAAAAAAAAAA AAAAAAAAAA | 20 |
| mRNA_Puromycin | GGGCGAAUUAAGAGAGAAAAGAAGAGUAAGAAGAAAUAUAA GACACCGGUCGCCACCAUGACCGAGUACAAGCCCACGGUGC GCCUCGCCACCCGCGACGACGUCCCCCGGGCCGUACGCACC CUCGCCGCCGCGUUCGCCGACUACCCCGCCACGCGCCACAC CGUCGAUCCGGACCGCCACAUCGAGCGGGUCACCGAGCUGC AAGAACUCUUCCUCACGCGCGUCGGGCUCGACAUCGGCAAG GUGUGGGUCGCGGACGACGGCGCCGCGGUGGCGGUCUGGA CCACGCCGGAGAGCGUCGAAGCGGGGGCGGUGUUCGCCGA GAUCGGCCCGCGCAUGGCCGAGUUGAGCGGUUCCCGGCUG GCCGCGCAGCAACAGAUGGAAGGCCUCCUGGCGCCGCACCG GCCCAAGGAGCCCGCGUGGUUCCUGGCCACCGUCGGCGUCU CGCCCGACCACCAGGGCAAGGGUCUGGGCAGCGCCGUCGUG CUCCCCGGAGUGGAGGCGGCCGAGCGCGCCGGGGUGCCCG CCUUCCUGGAGACCUCCGCGCCCCGCAACCUCCCCUUCUAC GAGCGGCUCGGCUUCACCGUCACCGCCGACGUCGAGGUGCC CGAAGGACCGCGCCACCUGGUGCAUGACCCGCAAGCCCGGUG CCUGAUCUAGACCUUCUGCGGGGCUUGCCUUCUGGCCAUG CCCUUCUUCUCUCCCUUGCACCUGUACCUCUUGGUCUUUGA AUAAAGCCUGAGUAGGAAAAAAAAAAAAAAAAAAAAAAAAA AAAAAAAAAAAAAAAAAAAAAAAAAAAAAAAAAAAAAAAAAA AAAAAAAAAAAAAAAAAAAAAAAAAAAAAAAAAAAAAAAAAA AAAAAAAA | 21 |

A sorting method according to an embodiment of the present invention may comprise a step of introducing an miRNA-responsive mRNA and an optional control mRNA into a cell population. This step allows a target type of cell to be sortable from the cell population containing the target type of cell. Specifically, this step enables a desired type of cell to provide detectable signal information different from signal information of the other types of cell in the cell population containing two or more types of cell optionally including the target type of cell. In the below-described production protocols, the sorting step may further be carried out to selectively separate the target type of cell.

Endothelial Cell Sorting Method

As used herein, endothelial cells are squamous thin cells constituting the inner surface of a blood vessel and are not distinguished from endothelial precursor cells in the present invention. Endothelial cells used in the present invention may be continuously cultured to form a tubular structure. Preferably, the cells can take up acetylated low-density-lipoproteins (ac-LDL). The endothelial cells are characterized by expression of a marker including, without particular limitation, CD31, etc.

In the present invention, a nucleic acid sequence that is specifically recognized by an miRNA and is contained in an miRNA-responsive mRNA used for sorting an endothelial cell is preferably a nucleic acid sequence specifically recognized by miR-126-3P or miR-126-5P.

A cell population that is subject to sorting may contain any cell population that can contain endothelial cells. For instance, the cell population may be a cell population that has been induced to differentiate from a pluripotent stem cell or may be an in vivo cell population, but is not limited thereto. Thus, it may be possible that an miRNA-responsive mRNA is introduced into a cell population that may or may not contain endothelial cells. In a preferable embodiment, the cell population may be a cell population that has been induced to differentiate from a pluripotent stem cell. Such induced differentiation is not limited to specific induction into endothelial cells, and may include induced differentiation for the purpose of obtaining another type of cell such as cardiomyocytes.

A protocol for producing endothelial cells from a pluripotent stem cell may be appropriately performed, including, for example, the known procedure (Li et al., J. Cell Biochem., 106: 194-199, 2009).

Hepatocyte Sorting Method

As used herein, hepatocytes are defined as cells expressing an mRNA of albumin or HNF4A. According to another embodiment of the present invention, hepatocytes are defined as cells characterized by any one or combination of known hepatocyte functions such as glycogen accumulation, low-density-lipoprotein (LDL) incorporation, albumin secretion, ammonia metabolism and urea synthesis, cytochrome P450 activity, lipid metabolism, and drug metabolism.

In the present invention, a nucleic acid sequence that is specifically recognized by an miRNA and is contained in an miRNA-responsive mRNA used for sorting a hepatocyte is preferably a nucleic acid sequence specifically recognized by miR-122-5P.

A cell population that is subject to sorting may contain any cell population that can contain hepatocytes. For instance, the cell population may be a cell population that has been induced to differentiate from a pluripotent stem cell or may be an in vivo cell population, but is not limited thereto. Thus, it may be possible that an miRNA-responsive mRNA is introduced into a cell population that may or may not contain hepatocytes. In a preferable embodiment, the cell population may be a cell population that has been induced to differentiate from a pluripotent stem cell. Such induced differentiation is not limited to specific induction into hepatocytes.

A protocol for producing hepatocytes from a pluripotent stem cell may be appropriately performed, including the known procedures (e.g., WO2001/081549; Takayama K, et al., Stem Cell Reports. 1: 322-335, 2013; Kajiwara M, et al., Proc Natl Acad Sci USA. 109: 12538-12543, 2012; Hay D C, et al., Stem Cells. 26: 894-902, 2008).

Insulin-Producing Cell Sorting Method

As used herein, insulin-producing cells are defined as cells expressing an mRNA of insulin.

In the present invention, a nucleic acid sequence that is specifically recognized by an miRNA and is contained in an miRNA-responsive mRNA used for sorting an insulin-producing cell is preferably a nucleic acid sequence specifically recognized by miR-375.

A cell population that is subject to sorting may contain any cell population that can contain insulin-producing cells. For instance, the cell population may be a cell population that has been induced to differentiate from a pluripotent stem cell or may be an in vivo cell population, but is not limited thereto. Thus, it may be possible for an miRNA-responsive mRNA to be introduced into a cell population that may or may not contain insulin-producing cells. In a preferable embodiment, the cell population may be a cell population that has been induced to differentiate from a pluripotent stem cell. Such induced differentiation is not limited to specific induction into insulin-producing cells.

Examples of a protocol for inducing insulin-producing cells from a pluripotent stem cell include methods for induced differentiation using activin and/or retinoic acid (RA) (Japanese Patent Laid-Open No. 2009-225661, E. Kroon et al., Nature Biotechnology (2008) Vol. 26, No. 4: 443-452, K. A. D'Amour et al., Nature Biotechnology (2006) Vol. 24, No. 11: 1392-1401, W. Jiang, Cell Research (2007) 17: 333-344, J. H. Shim et al., Diabetologia (2007) 50: 1228-1238, R. Maehra et al., PNAS (2009), vol. 106, No. 37: 15768-15773). Additional examples include: methods including introducing PDXI into a pluripotent stem cell and culturing the cell (U.S. Pat. No. 7,534,608 and Japanese Patent Laid-Open No. 2006-075022); and methods for producing insulin-producing cells by applying a suitable combination of low-molecular-weight compounds to a pluripotent stem cell (WO2011/081222 and Kunisada Y et al., Stem Cell Res. (2012) vol. 8, No. 2: 274-284).

Pluripotent Stem Cell

As used herein, a pluripotent stem cell is a stem cell that is pluripotent and can differentiate into many types of cells in vivo and can also self-replicate, and includes any type of cell that can be induced into hepatocytes used in the present invention. Examples of the pluripotent stem cell include, but are not particularly limited to, an embryonic stem (ES) cell, a nuclear transfer-mediated clone embryo-derived embryonic stem (ntES) cell, a germline stem cell ("GS cell"), an embryonic germ cell ("EG cell"), an induced pluripotent stem (iPS) cell, and a fibroblast or bone marrow stem cell-derived pluripotent cell (Muse cell). A preferable pluripotent stem cell is an iPS cell and more preferably a human iPS cell from the viewpoint that the cell is available without destroying an embryo or an egg, etc., during production thereof.

(A) Embryonic Stem Cell

An embryonic stem cell (ES cell) is a stem cell that has been established from an inner cell mass of an early embryo (e.g., a blastocyst) of a mammal such as a human and a mouse and that is pluripotent and can self-replicate.

The ES cell is an embryonic stem cell derived from an inner cell mass of a blastocyst, an embryo after an 8-cell stage and morula of a fertilized egg, and has an ability to differentiate into all the cells constituting an adult body, what is called pluripotency, and can self-replicate. The ES cell was discovered in a mouse in 1981 (M. J. Evans and M. H. Kaufman (1981), Nature 292: 154-156). Later, ES cell lines were established in primates such as a human and a monkey (J. A. Thomson et al. (1998), Science 282: 1145-1147; J. A. Thomson et al. (1995), Proc. Natl. Acad. Sci. USA, 92: 7844-7848; J. A. Thomson et al. (1996), Biol. Reprod., 55: 254-259; J. A. Thomson and V. S. Marshall (1998), Curr. Top. Dev. Biol., 38: 133-165).

An ES cell can be established by isolating an inner cell mass from a blastocyst of a fertilized egg of a target animal and culturing the inner cell mass on a fibroblast feeder layer. The cells can be maintained by splitting the culture using a culture medium containing, for example, leukemia inhibitory factor (LIF) and basic fibroblast growth factor (bFGF). Human and monkey ES cells have been established and maintained in accordance with the procedures described in, for example, U.S. Pat. No. 5,843,780; Thomson J A, et al. (1995), Proc Natl. Acad. Sci. USA. 92: 7844-7848; Thomson J A, et al. (1998), Science. 282: 1145-1147; H. Suemori et al. (2006), Biochem. Biophys. Res. Commun., 345: 926-932; M. Ueno et al. (2006), Proc. Natl. Acad. Sci. USA, 103: 9554-9559; H. Suemori et al. (2001), Dev. Dyn., 222: 273-279; H. Kawasaki et al. (2002), Proc. Natl. Acad. Sci. USA, 99: 1580-1585; Klimanskaya I, et al. (2006), Nature. 444: 481-485.

As a culture medium for producing an ES cell, it is possible to use DMEM/F-12 culture medium supplemented with, for example, 0.1 mM 2-mercaptoethanol, 0.1 mM non-essential amino acids, 2 mM L-glutamine, 20% KSR, and 4 ng/ml bFGF. Then, the human ES cell can be maintained at 37° C. and 5% $CO_2$ under a humid atmosphere (H. Suemori et al. (2006), Biochem. Biophys. Res. Commun., 345: 926-932). In addition, the ES cells should be divided every 3 to 4 days. At this time, the cells may be divided using, for example, 0.25% trypsin and 0.1 mg/ml collagenase IV in PBS containing 1 mM $CaCl_2$ and 20% KSR.

The ES cells can be selected, in general, by a real-time PCR method using, as an indicator, expression of gene markers such as alkaline phosphatase, Oct-3/4, and Nanog genes. Especially, human ES cells can be selected by using, as an indicator, expression of gene markers such as OCT-3/4, NANOG, and ECAD genes (E. Kroon et al. (2008), Nat. Biotechnol., 26: 443-452).

Regarding human ES cell lines, for example, WA01 (H1) and WA09 (H9) are available from WiCell Research Institute and KhES-1, KhES-2, and KhES-3 are available from the Institute for Frontier Medical Sciences, Kyoto University (Kyoto, Japan).

(B) Germline Stem Cell

The germline stem cell is a testis-derived pluripotent stem cell, which is a source of spermatogenesis. This cell, like the ES cell, can be induced to differentiate into various cell lineages, characterized in that when this cell is transplanted in a mouse blastocyst, for example, a chimeric mouse can be generated (M. Kanatsu-Shinohara et al. (2003) Biol. Reprod., 69:612-616; K. Shinohara et al. (2004), Cell, 119: 1001-1012). This cell can self-replicate in a culture medium containing glial cell line-derived neurotrophic factor (GDNF). In addition, after repeated cell passages under substantially the same culture conditions as of ES cells, a germline stem cell can be obtained (Masanori Takebayashi et al. (2008), "*Jikken Igaku* (Experimental Medicine)", vol. 26, no. 5 (special issue), pages 41-46, YODOSHA CO., LTD. (Tokyo, Japan)).

(C) Embryonic Germ Cell

The embryonic germ cell has been established from an embryonic primordial germ cell and, like an ES cell, is pluripotent. Also, an embryonic germ cell can be established by culturing a primordial germ cell in the presence of substances such as LIF, bFGF, and stem cell factor (Y. Matsui et al. (1992), Cell, 70: 841-847; J. L. Resnick et al. (1992), Nature, 359: 550-551).

(D) Induced Pluripotent Stem Cell

An induced pluripotent stem (iPS) cell can be created by introducing, as a form of DNA, RNA, or protein, specific reprogramming factors into a somatic cell, and is a somatic cell-derived induced stem cell that has substantially the same properties as of an ES cell, namely a cell having pluripotency and ability to self-replicate (K. Takahashi and S. Yamanaka (2006) Cell, 126: 663-676; K. Takahashi et al. (2007), Cell, 131: 861-872; J. Yu et al. (2007), Science, 318: 1917-1920; Nakagawa, M. et al., Nat. Biotechnol. 26:101-106 (2008); WO 2007/069666). The reprogramming factors may be composed of genes that are specifically expressed in an ES cell, the products or non-coding RNAs thereof, genes that play a critical role in keeping an ES cell undifferentiated, the products or non-cording RNAs thereof, and/or low-molecular-weight compounds. Examples of genes included in the reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tell, beta-catenin, Lin28b, Sall1, Sall4, Esrrb, Nr5a2, Tbx3 and Glis 1. These reprogramming factors may be used alone or in combination. The combinations of the reprogramming factors are exemplified and described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO 2010/056831, WO2010/068955, WO2010/098419, WO2010/102267, WO 2010/111409, WO 2010/111422, WO2010/115050, WO2010/124290, WO2010/147395, WO2010/147612, Huangfu D, et al. (2008), Nat. Biotechnol., 26: 795-797, Shi Y, et al. (2008), Cell Stem Cell, 2: 525-528, Eminli S, et al. (2008), Stem Cells. 26: 2467-2474, Huangfu D, et al. (2008), Nat Biotechnol. 26: 1269-1275, Shi Y, et al. (2008), Cell Stem Cell, 3, 568-574, Zhao Y, et al. (2008), Cell Stem Cell, 3: 475-479, Marson A, (2008), Cell Stem Cell, 3, 132-135, Feng B, et al. (2009), Nat Cell Biol. 11: 197-203, R. L. Judson et al., (2009), Nat. Biotech., 27: 459-461, Lyssiotis C A, et al. (2009), Proc Natl Acad Sci USA. 106: 8912-8917, Kim J B, et al. (2009), Nature. 461: 649-643, Ichida J K, et al. (2009), Cell Stem Cell. 5: 491-503, Heng J C, et al. (2010), Cell Stem Cell. 6: 167-74, Han J, et al. (2010), Nature. 463: 1096-100, Mali P, et al. (2010), Stem Cells. 28: 713-720, Maekawa M, et al. (2011), Nature. 474: 225-9.

Regarding the reprogramming factors, examples of a factor that is used to increase the establishment efficiency include: histone deacetylase (HDAC) inhibitors [e.g., low-molecular-weight inhibitors such as valproic acid (VPA), trichostatin A, sodium butyrate, MC 1293, M344; nucleic acid expression inhibitors such as siRNAs and shRNAs against HDAC (e.g., HDAC1 siRNA Smartpool (a registered trademark) (Millipore), HuSH 29mershRNA Constructs against HDAC1 (OriGene))]; MEK inhibitors (e.g., PD184352, PD98059, U0126, SL327, and PD0325901); glycogen synthase kinase-3 inhibitors (e.g., Bio and CHIR99021); DNA methyltransferase inhibitors (e.g., 5-azacytidine); histone methyltransferase inhibitors (e.g., low-molecular-weight inhibitors such as BIX-01294; nucleic acid expression inhibitors such as siRNAs and shRNAs against Suv39h1, Suv39h2, SetDB1, and G9a); L-channel calcium agonists (e.g., Bayk8644); butyric acid; TGF-β inhibitors or ALK5 inhibitors (e.g., LY364947, SB431542, 616453, and A-83-01); p53 inhibitors (e.g., siRNAs and shRNA against p53); ARID3A inhibitors (e.g., siRNAs and shRNAs against ARID3A); miRNAs such as miR-291-3p, miR-294, miR-295, and mir-302; Wnt signaling molecules (e.g., soluble Wnt3a); neuropeptide Y; prostaglandins (e.g., prostaglandin E2 and prostaglandin J2); and hTERT, SV40LT, UTF1, IRX6, GLIS1, PITX2, and DMRTB1. As used herein, unless otherwise indicated, these factors that are used to improve the establishment efficiency are included in the reprogramming factors.

The reprogramming factors may be introduced into a somatic cell by using technology such as lipofection, fusion to a cell penetrating peptide (e.g., HIV-derived TAT and polyarginine), and microinjection in the form of protein.

In the case of using a DNA form, examples of a technique used to introduce the reprogramming factors into a somatic cell include use of vectors (e.g., a virus, a plasmid, an artificial chromosome), lipofection, liposome, and microinjection. Examples of the virus vector include a retrovirus vector, a lentivirus vector (e.g., Cell, 126, pp. 663-676, 2006; Cell, 131, pp. 861-872, 2007; Science, 318, pp. 1917-1920, 2007), an adenovirus vector (Science, 322, 945-949, 2008), an adeno-associated virus vector, and a sendaivirus vector (WO 2010/008054). Examples of the artificial chromosome vector include a human artificial chromosome (HAC), a yeast artificial chromosome (YAC), and a bacterial artificial chromosome (BAC, PAC). As the plasmid, plasmids for mammalian cells may be used (Science, 322:949-953, 2008). In order to be able to express nuclear reprogramming substances, the vector may contain a promoter, an enhancer, a ribosome binding sequence, a terminator, a poly-A site. Also, the vector, if needed, may further contain: a drug resistance gene (e.g., a kanamycin resistant gene, an ampicillin resistance gene, a puromycin resistance gene); a selection marker sequence (e.g., a thymidine kinase gene, a diphtheria toxin gene); and/or a reporter gene sequence (e.g., genes encoding green fluorescent protein, β-glucuronidase (GUS), FLAG). In addition, to remove a reprogramming factor-encoding gene, or a promoter and a reprogramming factor-encoding gene linked to the promoter together after the introduction into a somatic cell, the vector may contain LoxP motifs before and after the sequence.

In the case of an RNA form, a technique such as lipofection and microinjection may be used to introduce the reprogramming factors into a somatic cell. To reduce their degradation, RNA containing 5-methylcytidine and pseudouridine (TriLink Biotechnologies) may be used (Warren L, (2010) Cell Stem Cell. 7: 618-630).

Examples of a culture medium for iPS cell induction include: 10 to 15% FBS-containing DMEM and DMEM/F12 or DME culture medium (these culture media optionally further containing LIF, penicillin/streptomycin, puromycin, L-glutamine, non-essential amino acids, β-mercaptoethanol, etc.); and commercially available culture media [e.g., mouse ES cell culture medium (TX-WES culture medium; Thromb-X N.V.), primate ES cell culture medium (primate ES/iPS cell culture medium; ReproCELL Inc.), serum-free media (mTeSR, Stemcell Technology, Inc.; Essential 8, Life Technologies, Inc.; StemFit, Ajinomoto, Inc.)].

For example, a culture protocol includes: causing reprogramming factors to contact somatic cells in 10% FBS-containing DMEM or DMEM/F12 culture medium at 37° C. in the presence of 5% $CO_2$ and culturing the cells for about 4 to 7 days, and thereafter; plating the cells on a feeder cell (e.g., mitomycin C-treated STO cell, SNL cell, etc.) layer; and culturing, from about 10 days after the contact between the somatic cells and the reprogramming factors, the resulting cells in bFGF-containing primate ES cell culture medium, so that iPS-like colonies can be generated at about 30 to about 45 days or later after the contact.

Alternatively, the relevant cells are cultured on a feeder cell (e.g., mitomycin C-treated STO cell, SNL cell, etc.) layer in 10% FBS-containing DMEM culture medium (further optionally containing LIF, penicillin/streptomycin, puromycin, L-glutamine, non-essential amino acids, β-mercaptoethanol, etc.) at 37° C. in the presence of 5% $CO_2$, so that ES-like colonies can be generated after about 25 to about 30 days or later. In a desirable protocol, instead of the feeder cells, for example, somatic cells that are subject to reprogramming are used (Takahashi K, et al. (2009), PLoS One. 4: e8067 or WO2010/137746) or an extracellular matrix (e.g., Laminin-5 (WO2009/123349), Matrigel (BD, Inc.), or iMatrix511 (Nippi, Inc.)) is used.

Other examples include a culturing protocol using a serum-free medium (Sun N, et al. (2009), Proc Natl Acad Sci USA. 106:15720-15725). In addition, to increase the establishment efficiency, an iPS cell may be established in a low oxygen condition (i.e., the level of oxygen of from 0.1% or more to 15% or less) (Yoshida Y, et al. (2009), Cell Stem Cell. 5: 237-241 or WO2010/013845)

During the culturing, the culture medium is changed to a fresh medium once a day from day 2 after initiation of the culture. In addition, the number of somatic cells used for nuclear reprogramming has no limitation and ranges from about $5 \times 10^3$ to about $5 \times 10^6$ cells per 100 $cm^2$ culture dish.

The iPS cell can be selected in accordance with the morphology of a colony formed. In addition, the iPS cell can be selected using, as indicators, genes (e.g., SSEA-1, SSEA-3, SSEA-4, TRA-2-54, TRA-1-60, and TRA-1-80) that are expressed when somatic cells are reprogrammed.

As used herein, the term "somatic cell" refers to any animal cell (preferably, mammalian cells, including human cells) excluding reproductive cells (e.g., an egg cell, an oocyte, an ES cell) or totipotent cells. Examples of the somatic cell include, without limitation, any of fetal somatic cells, neonatal somatic cells, and mature, healthy or disease somatic cells. Additional examples include any of primary culture cells, subcultured cells, and cell lines. Specific examples of the somatic cell include: (1) tissue stem cells (somatic stem cells) such as a neural stem cell, a hematopoietic stem cell, a mesenchymal stem cell, a dental pulp stem cell; (2) tissue precursor cells; and (3) differentiated cells such as a lymphocyte, an epithelial cell, an endothelial cell, a myocyte, a fibroblast (e.g., a skin cell, etc.), a hair cell, a hepatocyte, a gastric mucosa cell, an intestinal cell, a splenocyte, a pancreatic cell (e.g., a pancreatic exocrine cell, etc.), a brain cell, a pneumocyte, a nephrocyte, and an adipocyte.

Meanwhile, when the iPS cells are used as a transplantable cell material, it is desirable from the viewpoint of there being no occurrence of rejection to use somatic cells having the same or substantially the same HLA genotype as of an individual that is subject to transplantation. Here, the term "substantially the same" means that the HLA genotype is matched to such an extent that the immune reaction against the transplanted cells can be suppressed by an immunosuppressive agent. For example, the somatic cells have an HLA genotype in which three gene loci: HLA-A, HLA-B, and HLA-DR are identical or four gene loci including an additional HLA-C are identical.

(E) ES Cell Derived from Nuclear Transfer-Mediated Clone Embryo

A nuclear transfer-mediated clone embryo-derived ES cell (nt ES cell) is an ES cell that is derived from a clone embryo generated using a nuclear transfer technique and has substantially the same properties as of a fertilized egg-derived ES cell (T. Wakayama et al. (2001), Science, 292:740-743; S. Wakayama et al. (2005), Biol. Reprod., 72:932-936; J. Byrne et al. (2007), Nature, 450:497-502). That is, the nt ES (nuclear transfer ES) cell is an ES cell that has been established from an inner cell mass of a blastocyst of a clone embryo as obtained by switching the nucleus of an unfertilized egg to the nucleus of a somatic cell. To generate an nt ES cell, a nuclear transfer technique (J. B. Cibelli et al. (1998), Nature Biotechnol., 16:642-646) and ES cell creation technology are combined (Sayaka Wakayama (2008), "*Jikken Igaku* (Experimental Medicine)", vol. 26, no. 5 (special issue), pages 47-52). During the nuclear transfer, the nucleus of a somatic cell is injected into an enucleated unfertilized egg of a mammal and the resulting egg is cultured for reprogramming for several hours.

(F) Multilineage-Differentiating Stress Enduring Cell

The multilineage-differentiating stress enduring cell (Muse cell) is a pluripotent stem cell as generated by the protocol described in WO2011/007900. Specifically, fibroblasts or bone marrow stromal cells are treated with trypsin for an extended period and, preferably, the cells are treated for 8 or 16 h; and the cells are then subjected to suspension culture to yield pluripotent cells that are positive for SSEA-3 and CD105.

Cells sorted by the present invention may be administered pharmaceutically. Hence, provided is a therapeutic agent containing cells sorted by a method of the present invention. When the cells sorted are endothelial cells, the cells may be administered for treatment of patients with severe ischemia including coronary artery disease and lower limb ischemia (e.g., Buerger disease, arteriosclerosis obliterans, etc.). Hence, an embodiment of the present invention provides a vascular regeneration promoter containing endothelial cells sorted by the above-described method. When the cells sorted are hepatocytes, the cells may be administered for treatment of liver failure such as chronic liver failure (e.g., hepatic cirrhosis) and acute liver failure. Hence, an embodiment of the present invention provides a liver disease drug containing hepatocytes obtained by the above-described method. When the cells sorted are insulin-producing cells, the cells may be administered for treatment of diabetes mellitus, in particular, type I diabetes. Hence, an embodiment of the present invention provides a diabetes drug containing insulin-producing cells obtained by the above-described method. The number of cells administered has no particular limitation as long as the dose can exert an advantageous effect on treatment. The cells may be prepared by appropriately adjusting the number depending on the size of a lesion and/or the body size.

Example 1 miRNA Switch Construction
PCR Primers

Table 7 lists PCR primers used below.

TABLE 7

| Primer name | Sequence (5' -> 3') |
|---|---|
| TagBFP_Tfwd | GCCACCATGGGATCCAGCGAGCTGATTAAGGAGAAC |
| TagBFP_Trev | ACTCGAGATCTGTGCCCCAGTTTGCTAG |
| pGEMTAP_MCS_Rev | GGGATCCCATGGTGTCGACCTGCAGCATATGAGCTCCTGAATTCGCCCTATAGTGAGTCG |
| pGEMTAP_MCS_Fwd | GGGAGATCTCATATGCATCTCGAGTGATAGTCTAGACAAGCTTGAGTATTCTATAGTGTCACC |
| YF128_EXFP_Tfwd | GAACCATGGGATCCGTGAGCAAGGGCGAGG |
| YF129_EXFP_Trev | TATGAGATCTCTTGTACAGCTCGTCCATG |
| tagBFP fwd | CACCGGTCGCCACCATGGGATCCAGCGAG |
| TAPEGFP_IVTfwd | CACCGGTCGCCACCATGGGATCCGTGAGCAAGGGC |
| TAP_IVTrev | GCCCCGCAGAAGGTCTAGACTATCACTCGAGATGCATATGAGATC |
| TAP_T7_G3C fwd primer | CAGTGAATTGTAATACGACTCACTATAGGGC |
| Rev5UTR primer | CATGGTGGCGACCGGTGTCTTATATTTCTTCTTACTC |
| Fwd3UTR primer | TCTAGACCTTCTGCGGGGC |
| Rev3UTR2T20 | TTTTTTTTTTTTTTTTTTTTCCTACTCAGGCTTTATTCAAAGACCAAG |
| 3UTR120A rev primer | TTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTCCTACTCAGGCTTATTCA |

Template Plasmid DNA
(a) pTAP-tagBFP

A fragment was amplified by PCR method using pTagBFP-Tubulin (evrogen) as a template and TagBFP_Tfwd and TagBFP_Trev as primers. The resulting fragment was inserted into pGEM-TAP, a cloning vector originally constructed by the inventors. The pGEM-TAP was constructed by PCR mutagenesis using pGEM-Teasy (Promega) as a template and pGEMTAP_MCS_Rev and pGEMTAP_MCS_Fwd as primers.

(b) pCTp-EGFP

A fragment was amplified by PCR method using pEGFP-N1 (Clontech) as a template and YF128_EXFP_Tfwd and YF129_EXFP_Trev as primers. The resulting fragment was inserted into pCM-TAP, a cloning vector originally constructed by the inventors. The pCM-TAP was constructed by ligating a DraI-digested fragment of the above pGEM-TAP and a blunt-ended fragment of a NheI and AgeI-digested pLysSRARE2 (Novagen).

Construction of Sequence Containing Nucleic Acids Corresponding to Fluorescent Protein-Encoding Gene
(a) tagBFP A fragment was amplified by PCR using KOD-Plus-Neo (KOD-401, TOYOBO), the pTAP-tagBFP as a template, and tagBFP fwd and TAP_IVTrev as primers in a solution of Table 8 as prepared in accordance with manufacturer's instructions.

TABLE 8

| Component | Final concentration |
|---|---|
| 10 × kod-plus-Neo buffer | 1× |
| 2 mM dNTPs | 200 μM |
| 25 mM MgSO$_4$ aq | 1.5 mM |
| tagBFP fwd | 0.3 μM |
| TAP_IVTrev | 0.3 μM |
| pTAP-tagBFP | 1.0 ng/μL |
| 1 U/μL Kod+ polymerase | 0.02 U/μL |
| D2W | |
| Final volume | 50 μL |

The amplified PCR product was digested by DpnI (TOYOBO) at 37° C. for 30 min, and was then purified using a MiniElute PCR purification kit (QIAGEN) in accordance with manufacturer's instructions (to yield what is called a tagBFP PCR product).

(b) EGFP

In the same manner as (a), a fragment was amplified by PCR using the pCTp-EGFP as a template and TAPEGFP_IVTfwd and TAP_IVTrev as primers. The PCR amplification was carried out and the resulting PCR product (called an EGFP PCR product) was purified.

Construction of 5'UTR and 3'UTR Sequences
(a) 5'UTR

A fragment was amplified by PCR using KOD-Plus-Neo (KOD-401, TOYOBO), the IVT_5prime_UTR, which is shown in Table 10, as a template, and TAP_T7_G3C fwd primer and Rev5SUTR primer as primers in a solution of Table 9 as prepared in accordance with manufacturer's instructions.

TABLE 9

| Component | Final concentration |
|---|---|
| 10 × kod-plus-Neo buffer | 1× |
| 2 mM dNTPs | 200 μM |
| 25 mM MgSO$_4$ aq | 1.5 mM |
| TAP_T7_G3C fwd primer | 0.3 μM |
| Rev5UTR primer | 0.3 μM |
| IVT_5prime_UTR | 1.0 ng/μL |
| 1 U/μL Kod+ polymerase | 0.02 U/μL |
| D2W | |
| Final volume | 50 μL |

TABLE 10

| olgo-DNA name | Sequence (5' -> 3') |
|---|---|
| IVT_5prime_UTR | CAGTGAATTGTAATACGACTCACTATAGGGCGAATTAAGAGAGAAAAGAAGAGTAAGAAGAAATATAAGACACCGGTCGCCACCATG |
| IVT_3prime_UTR | TCTAGACCTTCTGCGGGGCTTGCCTTCTGGCCATGCCCTTCTTCTCTCCCTTGCACCTGTACCTCTTGGTCTTTGAATAAAGCCTGAGTAGG |

The amplified PCR product was then purified using a MiniElute PCR purification kit (QIAGEN) in accordance with manufacturer's instructions (to yield what is called a 5'UTR PCR product).
(b) 3'UTR
In the same manner as (a), a fragment was amplified by PCR using IVT_3prime_UTR, which is shown in Table 10, as a template and Fwd3UTR primer and Rev3UTR2T20 as primers, and the resulting fragment was purified (to yield what is called a 3'UTR PCR product).

IVT_EGFP Template Construction
A fragment was amplified by PCR using KOD-Plus-Neo (KOD-401, TOYOBO), the above-described EGFP PCR product, 5' UTR PCR product and 3' UTR PCR product as templates, and TAP_T7_G3C fwd primer and 3UTR120A rev primer as primers in a solution of Table 11 as prepared in accordance with manufacturer's instructions.

TABLE 11

| Component | Final concentration |
|---|---|
| 10 × kod-plus-Neo buffer | 1× |
| 2 mM dNTPs | 200 μM |
| 25 mM MgSO₄ aq | 1.5 mM |
| TAP_T7_G3C fwd primer | 0.3 μM |
| 3UTR120A rev primer | 0.3 μM |
| EGFP PCR product | 0.2 ng/μL |
| 5'UTR PCR product | 10 nM |
| 3'UTR PCR product | 10 nM |
| 1 U/μL Kod+ polymerase | 0.02 U/μL |
| D2W | |
| Final volume | 50 μL |

The amplified PCR product was digested by DpnI (TOYOBO) at 37° C. for 30 min, and was then purified using a MiniElute PCR purification kit (QIAGEN) in accordance with manufacturer's instructions.

Construction of IVT (In Vitro Transcription) Template for miRNA-Responsive mRNA
The IVT template for an miRNA switch was amplified by PCR using KOD-Plus-Neo (KOD-401, TOYOBO), the above-described tagBFP PCR product, each miRNA target 5'UTR oligo-DNA, and the above-described 3' UTR PCR product as templates, and T7FwdB primer and 3UTR120A rev primer as primers in a solution of Table 12 as prepared in accordance with manufacturer's instructions. Table 13 lists each miRNA target 5' UTR oligo-DNA.

TABLE 12

| Component | Final concentration |
|---|---|
| 10 × kod-plus-Neo buffer | 1× |
| 2 mM dNTPs | 200 μM |
| 25 mM MgSO₄ aq | 1.5 mM |
| T7FwdB primer | 0.3 μM |
| 3UTR120A rev primer | 0.3 μM |

TABLE 12-continued

| Component | Final concentration |
|---|---|
| tagBFP PCR product | 0.2 ng/μL |
| miRNA target 5'UTR olgo-DNA | 10 nM |
| 3'UTR PCR product | 10 nM |
| 1 U/μL Kod+ polymerase | 0.02 U/μL |
| D2W | |
| Final volume | 50 μL |

TABLE 13

| oligo-DNA name | Sequence |
|---|---|
| 5UTRtemp_T208a-3p | CGACTCACTATAGGTTCCGCGATCGCGGATCCACAAGCTTTTTGCTCGTCTTATAGATCACACCGGTCGCCACCATG |
| 5UTRtemp_T10b-5p | CGACTCACTATAGGTTCCGCGATCGCGGATCCCACAAATTCGGTTCTACAGGGTAAGATCCACCGGTCGCCACCATG |
| 5UTRtemp_T126-3p | CGACTCACTATAGGTTCCGCGATCGCGGATCCCGCATTATTACTCACGGTACGAAGATCACACCGGTCGCCACCATG |
| 5UTRtemp_T126a-5p atog | CGACTCACTATAGGTTCCGCGATCGCGGATCCCGCGTACCAAAAGTAATAGTGAGATCAACACCGGTCGCCACCATG |
| 5UTRtemp_T196b-5p | CGACTCACTATAGGTTCCGCGATCGCGGATCCCCCAACAACAGGAAACTACCTAAGATCACACCGGTCGCCACCATG |
| 5UTRtemp_T216a-5p | CGACTCACTATAGGTTCCGCGATCGCGGATCCTCACAGTTGCCAGCTGAGATTAAGATCACACCGGTCGCCACCATG |
| 5UTRtemp_T126-3p + T208a-3p | CGACTCACTATAGGTTCCGCGATCGCGGATCCCGCATTATTACTCACGGTACGAACAAGCTTTTTGCTCGTCTTATAGATCACACCGGTCGCCACCATG |
| 5UTRtemp_T126-5p + T208a-3p | CGACTCACTATAGGTTCCGCGATCGCGGATCCCGCGTACCAAAAGTAATAGTGAACAAGCTTTTTGCTCGTCTTATAGATCACACCGGTCGCCACCATG |
| 5UTRtemp_T208a-3p + T126-3p | CGACTCACTATAGGTTCCGCGATCGCGGATCCACAAGCTTTTTGCTCGTCTTATCGCATTATTACTCACGGTACGAAGATCACACCGGTCGCCACCATG |
| 5UTRtemp_T208a-3p + T126-5p | CGACTCACTATAGGTTCCGCGATCGCGGATCCACAAGCTTTTTGCTCGTCTTATCGCGTACCAAAAGTAATAGTGAAGATCACACCGGTCGCCACCATG |
| 5UTRtemp_T122-3p | CGACTCACTATAGGTTCCGCGATCGCGGATCCATATTTAGTGTGATAATGGCGTTAGATCCACCGGTCGCCACCATG |
| 5UTRtemp_T122-5p | CGACTCACTATAGGTTCCGCGATCGCGGATCCCAAACACCATTGTCACACTCCAAGATCACACCGGTCGCCACCATG |
| 5UTRtemp_T192-5p | CGACTCACTATAGGTTCCGCGATCGCGGATCCGGCTGTCAATTCATAGGTCAGAGATCAACACCGGTCGCCACCATG |
| 5UTRtemp_T194-5p | CGACTCACTATAGGTTCCGCGATCGCGGATCCTCCACATGGAGTTGCTGTTACAAGATCACACCGGTCGCCACCATG |
| 5UTRtemp_T215 | CGACTCACTATAGGTTCCGCGATCGCGGATCCGTCTGTCAATTCATAGGTCATAGATCAACACCGGTCGCCACCATG |
| 5UTRtemp_T375 | CGACTCACTATAGGTTCCGCGATCGCGGATCCTCACGCGAGCCGAACGAACAAAAGATCACACCGGTCGCCACCATG |

The amplified PCR product was digested by DpnI (TOYOBO) at 37° C. for 30 min, and was then purified using a MiniElute PCR purification kit (QIAGEN) in accordance with manufacturer's instructions.

Synthesize and Production of mRNA
Each mRNA was produced using a MEGAscript T7 kit (Ambion) and each IVT template in accordance with the protocol described in Warren L, et al., Cell Stem Cell. 7(5): 618-30 (2010). In this reaction, pseudouridine-5'-triphosphate and methylcytidine-5'-triphosphate (TriLink BioTechnologies) were used as alternatives for uridine triphosphate and cytidine triphosphate, respectively. Before the IVT (mRNA synthesis) reaction, guanidine-5'-triphosphate was diluted five-fold with Anti-Reverse Cap Analog (New England Biolabs). The reaction mixture was incubated at 37° C. for 5 h, TURBO DNase (Ambion) was added, and the resulting mixture was then further incubated at 37° C. for 30 min. The resulting mRNA was purified through FavorPrep Blood/Cultured Cells total RNA extraction column (Favorgen Biotech), and was incubated with Antarctic phosphatase (New England Biolabs) at 37 C° for 30 min. After that, the mRNA was further purified using an RNeasy Mini Elute Cleanup kit (QIAGEN).

Example 2

Endothelial Cell Isolation
HUVECs Culture

Figure 1B:
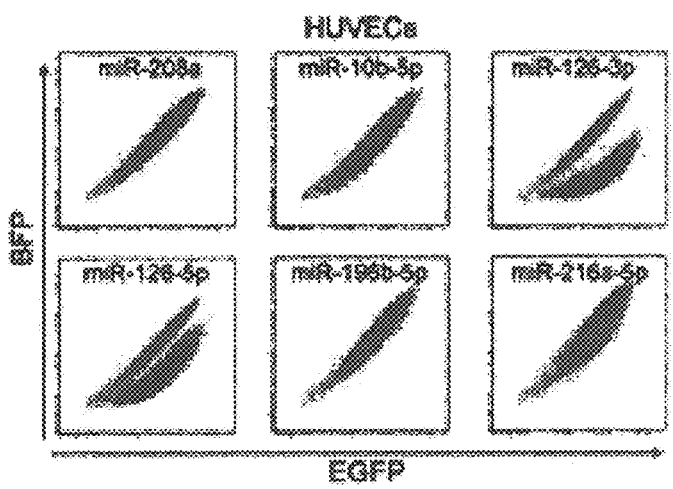
FIG. 1B shows the flow cytometry analysis results obtained after each miRNA switch (containing miR-208, miR-0b-5p, miR-126-3p, miR-126-5p, miR-196b-5, and miR-216a5p) or BFP together with EGFP were introduced into HUVECs.
Figure 2A:
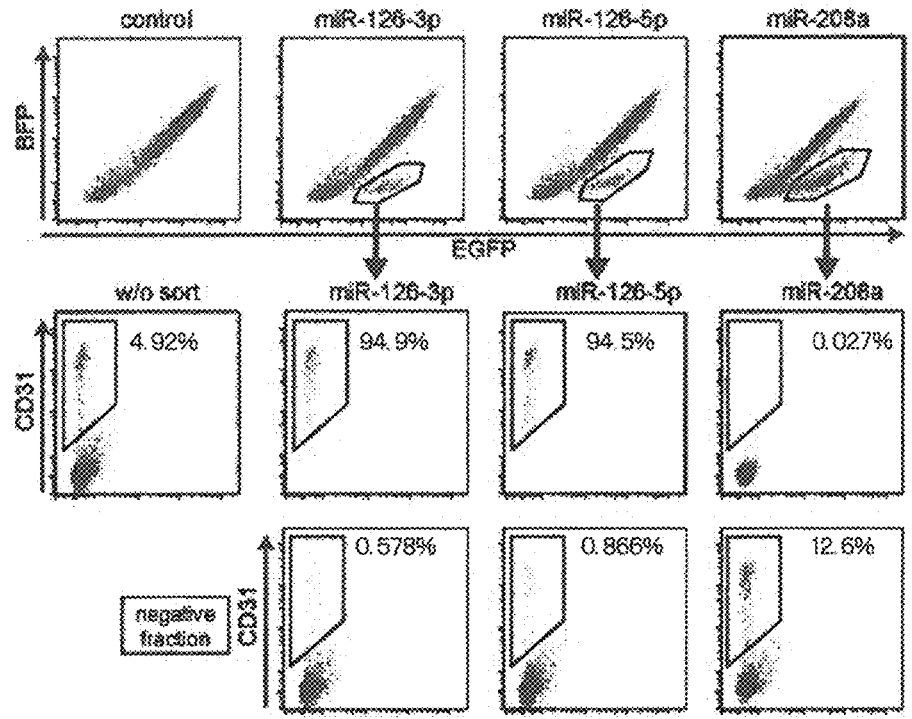
FIG. 2A shows the flow cytometry analysis results obtained after each miRNA switch (containing miR-208, miR-10b-5p, miR-126-3p, miR-126-5p, miR-196b-5, or miR-216a5p) together with EGFP was introduced into a cardiomyocyte population containing endothelial cells derived from induced differentiation of iPS cells.
Figure 2B:
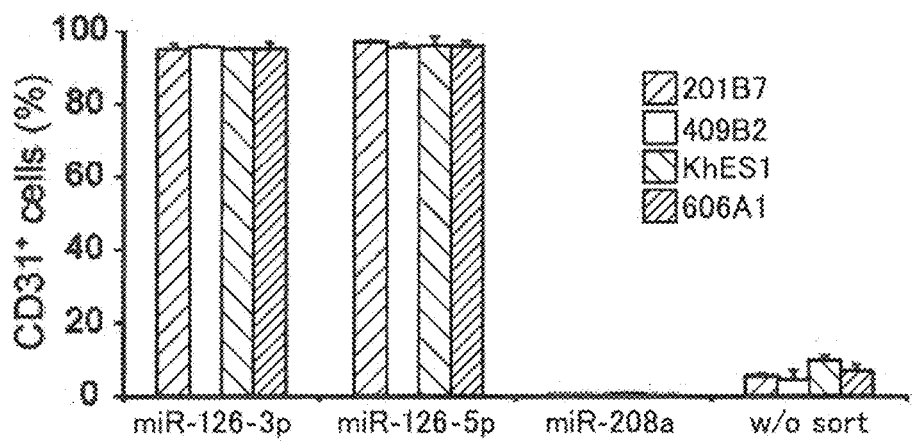
FIG. 2B is a graph showing the percentage of CD31-positive cells in cells sorted using each miRNA switch (miR-208, miR-126-3p, and miR-126-5p) from a cardiomyocyte population containing endothelial cells induced from each of iPS cells (201B7, 409B2, and 606A1) and ES cells (KhES1).
Figure 2C:
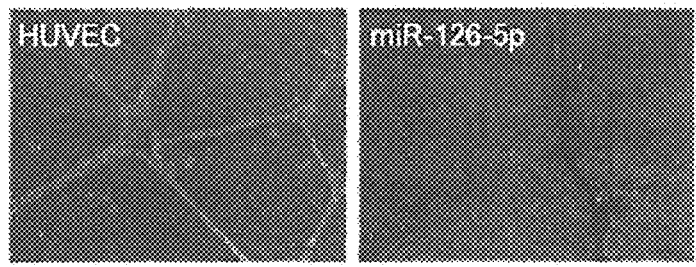
FIG. 2C shows the results of subjecting HUVEC or the cells, which were sorted using miR-126-5p miRNA switch, to tube formation assay.

Human umbilical vein endothelial cells (HUVECs) (C2517A) were purchased from Lonza, Inc., and were cultured using an EGM-2 Endothelial Cell Growth Medium-2 Bullet kit (Lonza).
Microarray Analysis The miRNA expression was profiled using Agilent Technologies Human miRNA Microarray Release 19.0 in accordance with the manufacturer's protocol. The data was analyzed using GeneSpring GX 12.6 software (Agilent Technologies).
Method for Inducing Cardiomyocytes Containing Endothelial Cells As human iPS cells, used was 201B7 cell line described in Takahashi K, et al. Cell. 131: 861-72, 2007, 409B2 (available from Riken BioResource Center), or 606A1 described in Okita K, et al., Stem Cells 31, 458-66, 2012. As human ES cells, KhES1 was used and obtained from Kyoto University. The human iPS cells or ES cells were treated with CTK solution (ReproCELL) for 2 min. Next, the solution was removed. Subsequently, the cells were treated with Accumax (Innovative Cell Technologies) for 5 min. Then, the cells were subjected to pipetting to single cells. The resulting cells were recovered by centrifugation, transferred to a low-attachment 6-well dish (Corning), and cultured at 37° C. under 5% oxygen condition in 1.5 ml/well of STEMPRO 34 (Invitrogen) supplemented with 2 mM L-glutamine, 150 µg/mL transferrin, 50 µg/mL ascorbic acid (sigma), $4\times10^{-4}$ M monothioglycerol (MTG), 0.5% penicillin/streptomycin (Invitrogen), 10 µM ROCK inhibitor (Y-27632), and 2 ng/mL BMP4 (R&D) to induce EB formation (day 0). Next day (day 1), to the 6-well plate wells having an EB culture was added an equal volume of STEMPRO 34 supplemented with 2 mM L-glutamine, 150 µg/mL transferrin, 50 µg/mL ascorbic acid, $4\times10^{-4}$ M MTG, 0.5% penicillin/streptomycin, 18 ng/mL BMP4 (at final concentration of 10 ng/ml), 10 ng/mL bFGF (at final concentration of 5 ng/ml), and 12 ng/mL Activin A (at final concentration of 6 ng/ml). The resulting culture was cultured at 37° C. under 5% oxygen condition for 3 days. Four days after the induction (day 4), the resulting EB was washed with IMDM (Invitrogen). To the dish was added STEMPRO 34 supplemented with 2 mM L-glutamine, 150 µg/mL transferrin, 50 µg/mL ascorbic acid, $4\times10^{-4}$ M MTG, 10 ng/mL VEGF, and 1 µM IWP-3 (Stemgent). The resulting culture was cultured at 37° C. under 5% oxygen condition for 4 days. Eight days after the induction (day 8), the medium was changed to STEMPRO 34 supplemented with 2 mM L-glutamine, 150 µg/mL transferrin, 50 µg/mL ascorbic acid, $4\times10^{-4}$ M MTG, 0.5% penicillin/streptomycin, 10 ng/mL VEGF, and 5 ng/mL bFGF. The resulting culture was cultured at 37° C. under 5% oxygen condition for 4 days. At this occasion, the medium change under the same conditions was performed once every two days. Twelve days after the induction (day 12), the culture was transferred to an incubator with a normal oxygen level and was further cultured for 8 days. At this occasion, the medium change under the same conditions was performed once every two days.
Tube Formation Assay The endothelial cells isolated were seeded at $2\times10^5$ cells/well on a Matrigel (BD)-coated 24-well plate, and were cultured in EGM-2 Bullet Kit medium. Next day, the culture was observed under a Biorevo BZ-9000 microscope.
Results To isolate endothelial cells, human umbilical vein endothelial cells (HUVECs) were used for microarray analysis; and top 5 miRNAs (hsa-miR-10b-5p, hsa-miR-126-3p, hsa-miR-126-5p, hsa-miR-196b-5p, and hsa-miR-216a-5p) specifically expressed in the endothelial cells were discovered (FIG. 1A). Next, miRNA switches, each having BFP and a sequence specifically recognized by each miRNA, (hereinafter, each referred to as miR-** miRNA switch) were constructed by the procedure described in Example 1 and each miRNA switch together with EGFP mRNA as a control was introduced into HUVECs. As a result, HUVECs of interest were successfully isolated using each of miR-126-3p miRNA switch and miR-126-5p miRNA switch (FIG. 1B). As a control, both BFP mRNA and EGFP mRNA were together introduced into HUVECs. This result was compared with the above result and the isolation was verified. Further, to check whether or not the miRNA switches were used to be able to isolate endothelial cells, the above protocol was applied to cardiomyocyte induction. Then, examined was whether it was possible to isolate endothelial cells contained in cells after the induction. The results demonstrated that a post-cardiomyocyte-induction cell population contained about 5 to 10% of cells capable of being isolated using the miR-126-3p miRNA switch and the miR-126-5p miRNA switch and the cells were positive for CD31, an endothelial marker (FIGS. 2A and 2B). By contrast, CD31-positive cells were unable to be isolated using miR-208a miRNA switch. Hence, it is suggested that the miR-126-3p miRNA switch and the miR-126-5p miRNA switch are useful in isolating endothelial cells from a heterogeneous cell population. Further, the cells that were isolated using the miR-126-5p miRNA switch were subjected to tube formation assay. The results demonstrated that the cells had angiogenic potential (FIG. 2C).

Figure 3A:
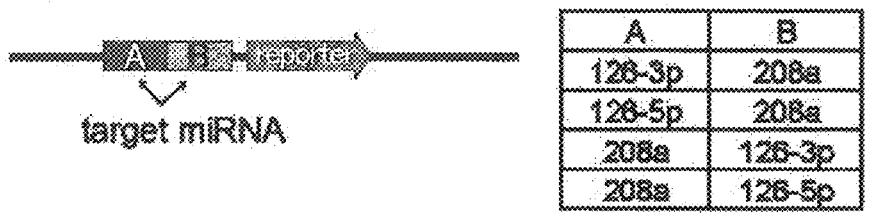
FIG. 3A is a schematic diagram illustrating an miRNA switch containing two target sequences.
Figure 3B:
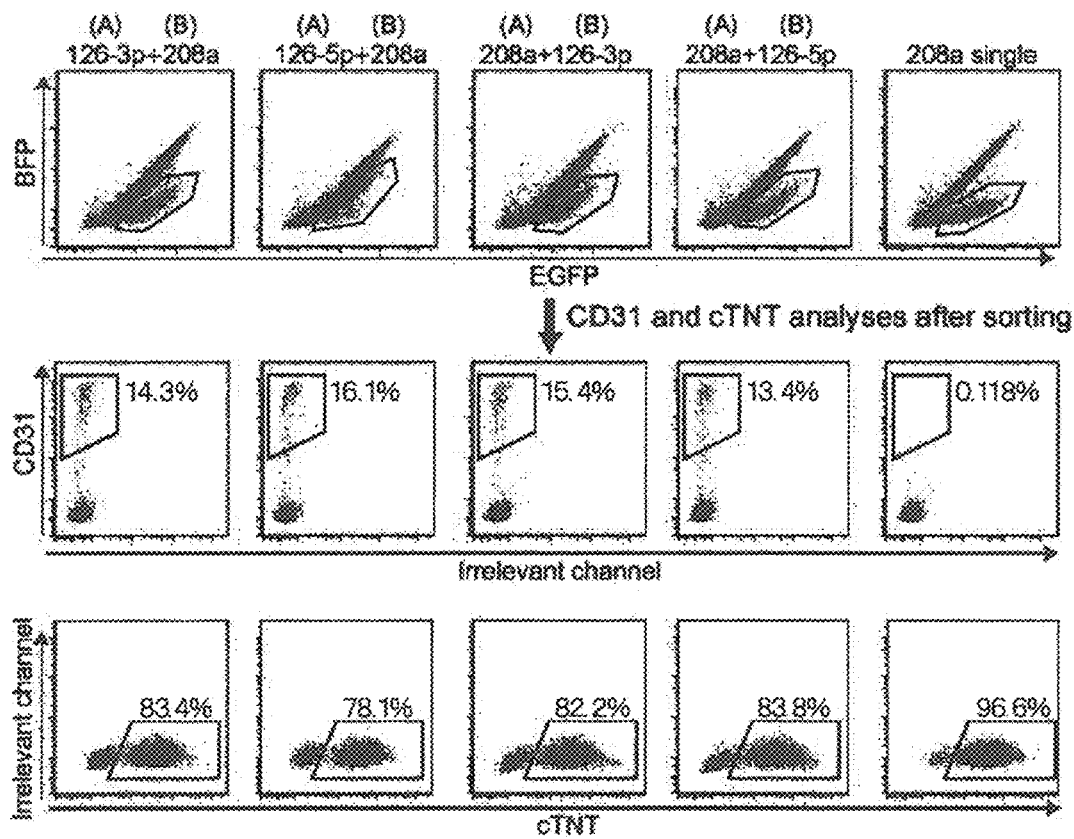
FIG. 3B is the flow cytometry analysis results showing the percentage of CD31-positive cells or cTnT-positive cells in cells sorted using each miRNA switch (miR-126-3p+miR-208, miR-126-5p+miR-208, miR-208+miR-126-3p, miR-208+miR-126-5p, and miR-208) from cardiomyocytes and endothelial cells induced from iPS cells.
Figure 3C:
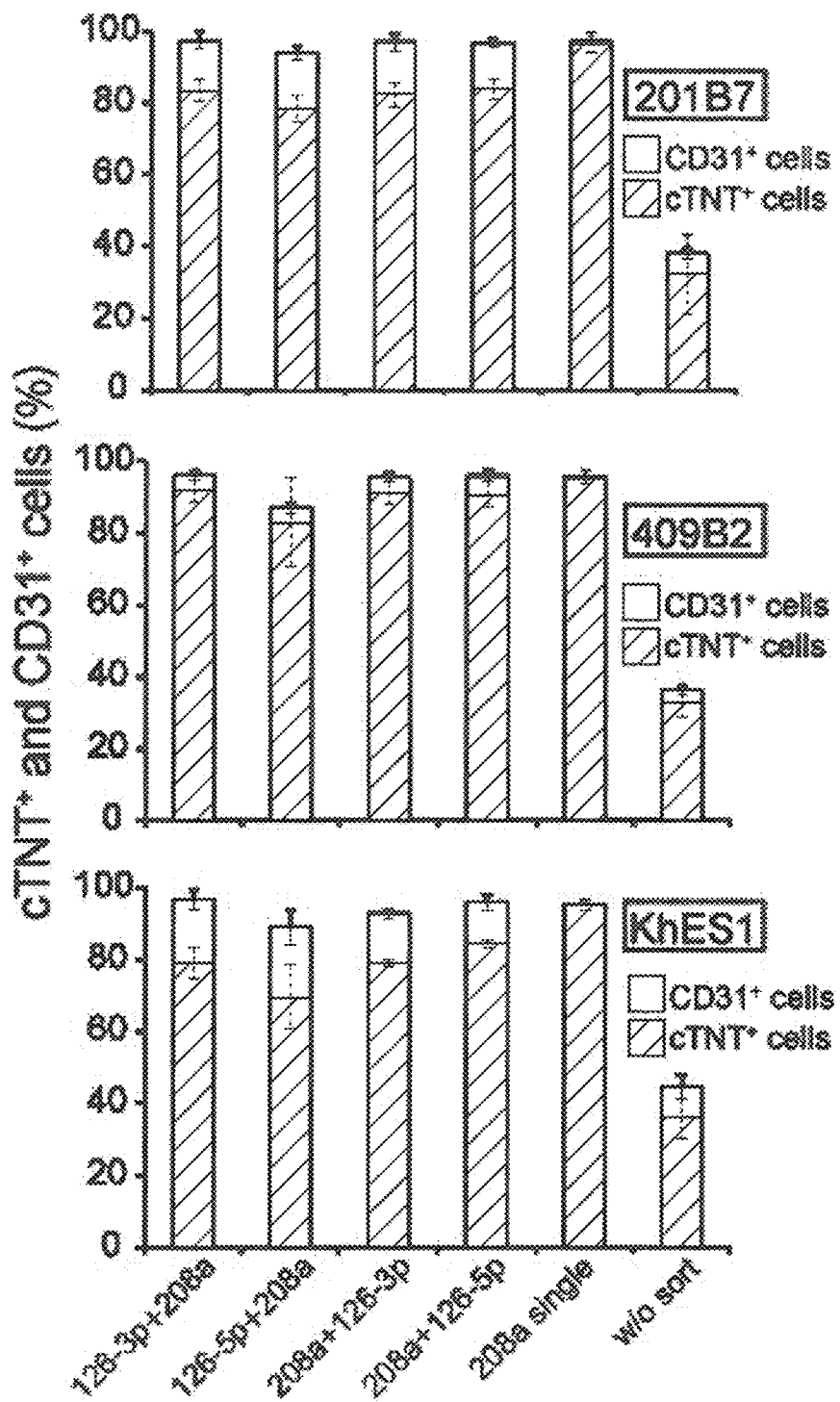
FIG. 3C has graphs each showing the percentage of CD31-positive cells or cTnT-positive cells in cells sorted using each miRNA switch (miR-126-3p+miR-208, miR-126-5p+miR-208, miR-208+miR-126-3p, miR-208+miR-126-5p, and miR-208) from cardiomyocytes and endothelial cells induced from each of iPS cells (20187 and 409B2) and ES cells (KhES1).

Next examined was whether or not cardiomyocytes and endothelial cells were able to be simultaneously isolated using an miRNA switch having sequences specificity recognized by two miRNAs specific to cardiomyocytes and endothelial cells. Specifically, 4 different miRNA switches, in which miR-208a, and miR-126-3p or miR-126-5p were used in combination, as described in FIG. 3A were constructed; each miRNA switch together with EGFP mRNA as a control was introduced into a cell population containing cardiomyocytes induced from iPS cells; and the fluorescent intensity of BFP, the percentage of CD31-positive cells, and the percentage of cTnT-positive cells were measured. The results demonstrated that cells positive for each marker were successfully isolated (FIGS. 3B and 3C). In addition, at that time, when a combination of miR-126-5p+miR-208a was used, a decrease in the level of fluorescent intensity of BFP was relatively strong.

Example 3

Hepatocyte Isolation
Hepatocytes Culture

Human primary hepatocytes were purchased from Bioreclamation IVT and were cultured in InVitroGRO CP Medium (Bioreclamation IVT) supplemented with Torpedo Antibiotic Mix (Bioreclamation IVT).

Method for Inducing Hepatocytes

As human iPS cells, used was 201B6 cell line described in Takahashi K, et al., Cell. 131: 861-72, 2007. Hepatocytes were induced from human iPS cells in accordance with the method, with a modification, described in Kajiwara M, et al., Proc Natl Acad Sci USA. 109: 12538-12543, 2012. Specifically, the human iPS cells were seeded on a Matrigel-coated plate. Next, to the plate was added RPMI 1640 medium supplemented with 1×B27 supplement, 100 ng/ml activin A, 10 µM Y-27632, and 1 µM CHIR99021. The next day (day 1), the medium was changed to a culture medium in which Y-27632 had been removed from and 0.5 mM NaB had been added to the above medium. On day 5, the medium was changed to knockout DMEM supplemented with 20% knockout serum replacement (KSR), 1 mM L-glutamine, 1% nonessential amino acids, 0.1 mM 2-mercaptoethanol, 1% DMSO, 10 ng/ml FGF, and 20 ng/ml BMP4, and the cells were cultured for 6 days. On day 11, the medium was changed to hepatocyte culture medium (Lonza) supplemented with 20 ng/ml hepatocyte growth factor (HGF) and 20 ng/ml oncostatin M (OSM). The culture mixture was further cultured for seven days to yield hepatocytes.

Results

Figure 4A:
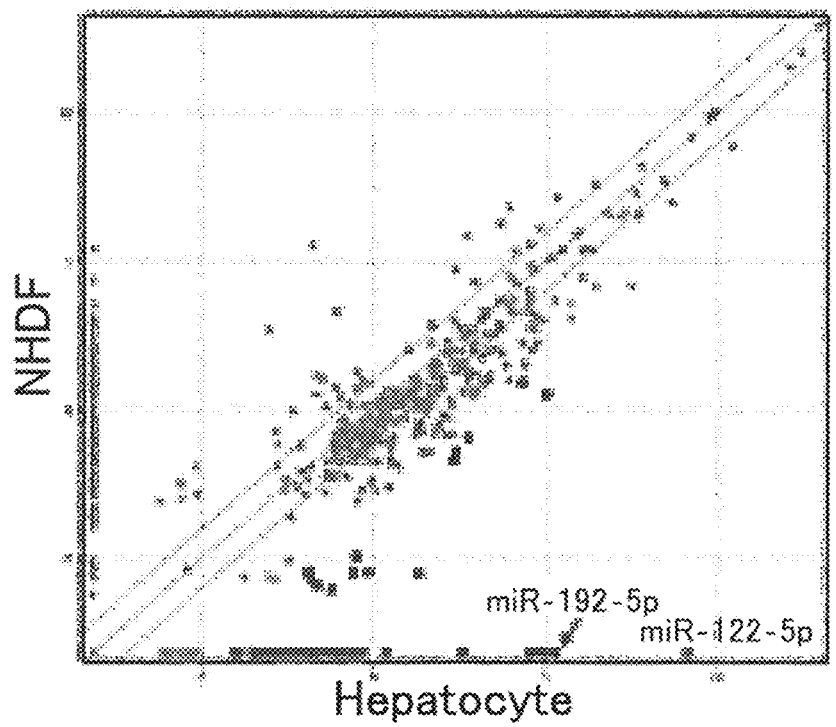
FIG. 4A shows the results of comparing, using a microarray, the levels of expression of miRNAs between primary hepatocytes and fibroblasts (NHDF).
Figure 4B:
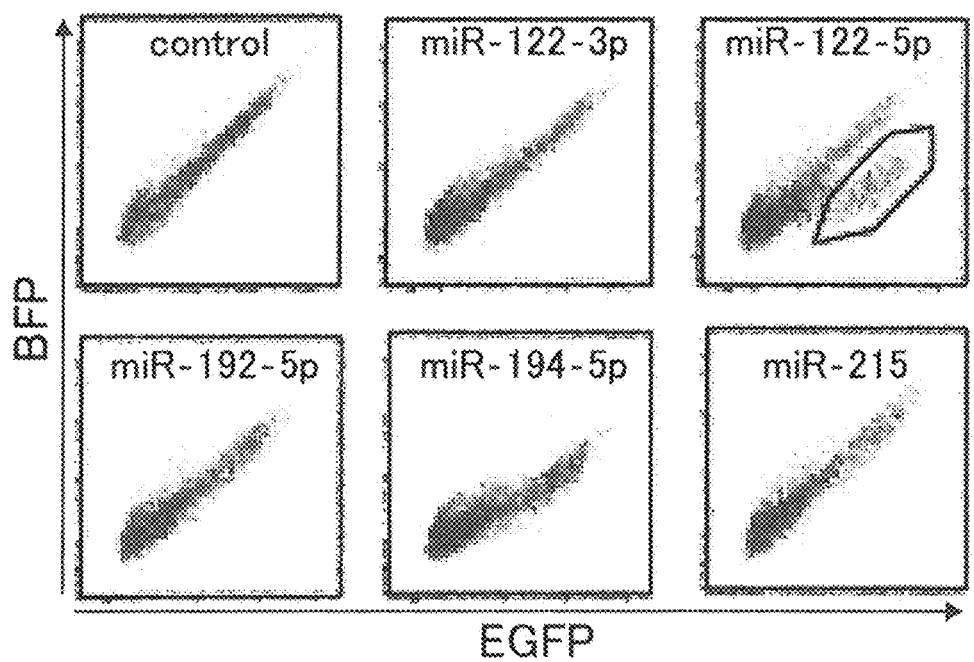
FIG. 4B shows the flow cytometry analysis results obtained after each miRNA switch (containing control, miR-122-3p, miR-122-5p, miR-192-5p, miR-194-5p, and miR-215) together with EGFP was introduced into a hepatocyte population derived from induced differentiation of iPS cells.
Figure 5A:
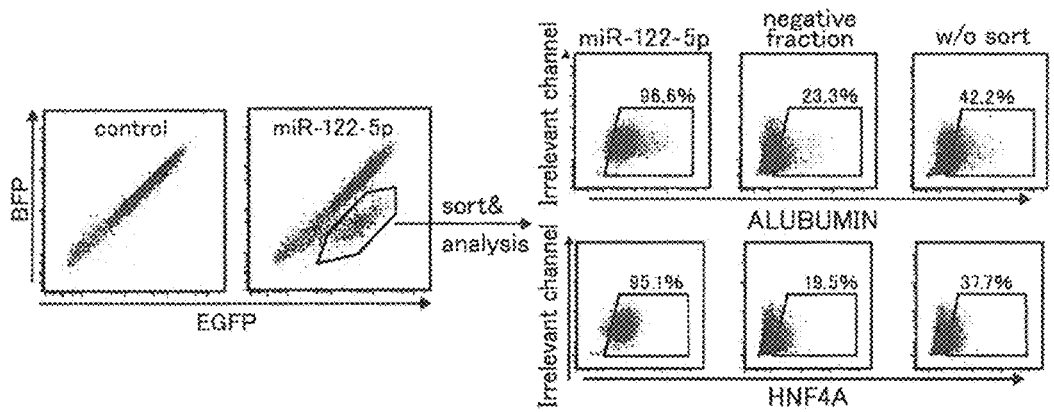
FIG. 5A shows the flow cytometry analysis results obtained after miR-122-5p miRNA switch together with EGFP was introduced into a hepatocyte population derived from induced differentiation of iPS cells.
Figure 5B:
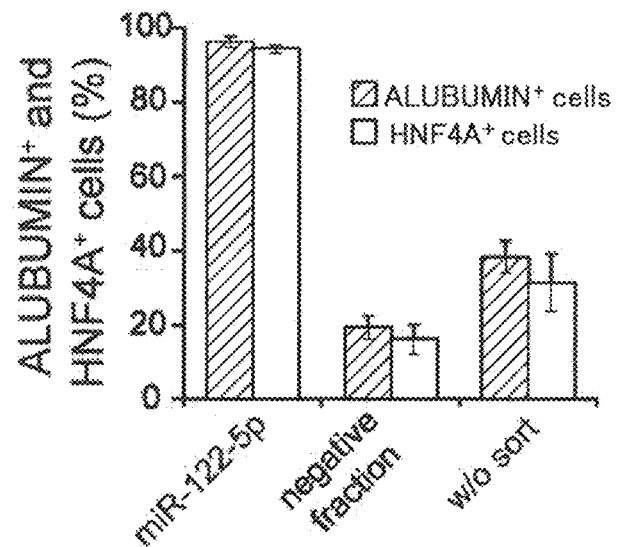
FIG. 5B is a graph showing the percentage of ALUBUMIN-positive cells or INF4A-positive cells in: cells sorted using miR-122-5p miRNA switch from a hepatocyte population derived from induced differentiation of iPS cells; cells (negative fraction) other than the cells sorted using the miR-122-5p miRNA switch; and a hepatocyte population (w/o sort) derived from induced differentiation of the iPS cells.
Figure 5C:
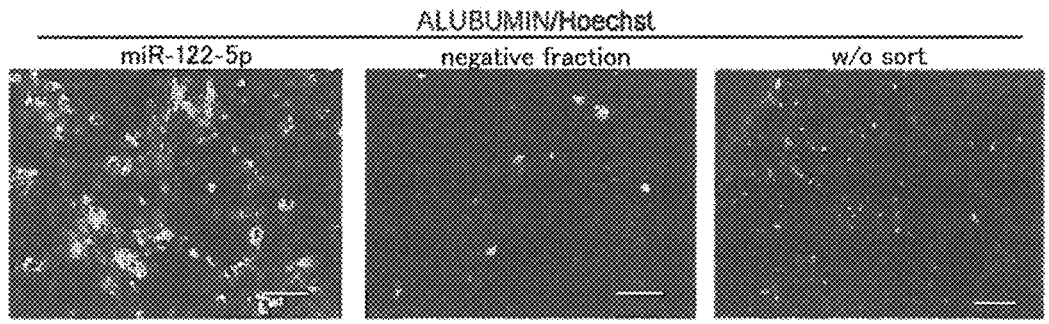
FIG. 5C shows the immunostaining results obtained by staining, with an anti-ALUBUMIN antibody, cells sorted using miR-122-5p miRNA switch from a hepatocyte population derived from induced differentiation of iPS cells; cells (negative fraction) other than the cells sorted using the miR-122-5p miRNA switch; and a hepatocyte population (w/o sort) derived from induced differentiation of the iPS cells.

To isolate hepatocytes, primary hepatocytes were used for microarray analysis; and top 5 miRNAs (hsa-miR-122-3p, hsa-miR-122-5p, hsa-miR-192-5p, hsa-miR-194-5p, and hsa-miR-215) specifically expressed in hepatocytes were discovered (FIG. 4A). Corresponding miRNA switches were constructed by the procedure of Example 1 and each miRNA switch together with EGFP mRNA as a control is introduced into hepatocytes derived from induced differentiation of human iPS cells. As a result, cells of interest were successfully isolated using miR-122-5p miRNA switch (FIG. 4B). Then, it was examined as to whether ALBUMIN and HNF4A were expressed in the cells isolated. The results demonstrated that the cells positive for both could be isolated (FIGS. 5A and 5B). Further, the cells that were isolated using miR-122-5p as an indicator were confirmed to be positive for ALBUMIN by immunostaining (FIG. 5C).

Example 4

Insulin-Producing Cell Isolation
Method for Inducing Insulin-Producing Cells

As human iPS cells, used was 585A1 cell line described in Okita K, et al., Stem Cells 31, 458-66, 2012. Insulin-producing cells were induced from human iPS cells in accordance with the process described in Kunisada Y, et al., Stem Cell Res. 8:274-284, 2012 and Nakagawa, M, et al., Sci Rep 4, 3594, 2014. Specifically, the cells were cultured for 1 day in RPMI 1640 medium supplemented with 1×B27 supplement, 10 µM Y-27632, and 3 µM CHIR99021. The next day (day 1), the medium was changed to RPMI 1640 medium containing 1×B27 supplement, 100 ng/ml activin A, and 1 µM CHIR99021, and the cells were cultured for 3 days. Subsequently, the medium was changed to Improved MEM Zinc Option medium supplemented with 0.5×B27 supplement, 1 µM dorsomorphin, 2 µM retinoic acid, and 10 µM SB431542, and the cells were cultured for 6 days. Further, the medium was changed to Improved MEM Zinc Option medium supplemented with 0.5×B27 supplement, 10 µM forskolin, 10 µM dexamethasone, 5 µM Alk5 inhibitor II, and 10 mM nicotinamide, and the cells were cultured for 8 days.

Results

According to the previous reports (Francis, N., et al., Microrna 3, 54-63, 2014; Lahmy, R., et al., Mol Biol Rep 41, 2055-2066, 2014; and Ozcan, S. Mol Endocrinol 28, 1922-1933, 2014), has-miR-375 was used as an miRNA specifically expressed in insulin-producing cells. First, miR-375 miRNA switch was constructed by the above procedure and the miR-375 miRNA switch together with EGFP mRNA as a control was introduced into insulin-producing cells derived from induced differentiation of human iPS cells. As a result, cells of interest were successfully isolated using the miRNA switch (FIGS. 6A and 6B). The cells isolated were confirmed to be positive for INSULIN by immunostaining (FIG. 6C).

The invention claimed is:

1. A method for producing insulin-producing cells, comprising:
   (a) producing, from a pluripotent stem cell, a cell population containing insulin-producing cells;
   (b) introducing, into the cell population of the step (a), an miRNA-responsive mRNA consisting of sequences comprising (i) a nucleic acid recognized specifically by miR-375 and (ii) a nucleic acid corresponding to a coding region of a first marker gene, wherein the miRNA-responsive mRNA is introduced into the cell population in a form of a synthetic RNA molecule; and
   (c) sorting a cell having a low level of translation of the first marker gene of the step (b).

2. The method according to claim 1, wherein the miRNA-responsive mRNA comprises a Cap structure and a polyA tail.

3. The method according to claim 1, wherein the nucleic acid recognized specifically by miR-375 is included in a 5' UTR or 3' UTR of the coding region of the first marker gene in the miRNA-responsive mRNA.

* * * * *

UNITED STATES PATENT AND TRADEMARK OFFICE
CERTIFICATE OF CORRECTION

| | |
|---|---|
| PATENT NO. | : 10,501,811 B2 |
| APPLICATION NO. | : 15/568209 |
| DATED | : December 10, 2019 |
| INVENTOR(S) | : Yoshida et al. |

It is certified that error appears in the above-identified patent and that said Letters Patent is hereby corrected as shown below:

In the Specification

Column 4, Line 5: Please correct "miR-0b-5p" to read -- miR-10b-5p --

Column 4, Line 39: Please correct "20187" to read -- 201B7 --

Column 26, Line 52: Please correct "Rev5SUTR" to read -- Rev5UTR --

Signed and Sealed this
Fifth Day of May, 2020

Andrei Iancu
*Director of the United States Patent and Trademark Office*

SEQUENCE LISTING

```
<160> NUMBER OF SEQ ID NOS: 21

<210> SEQ ID NO 1
<211> LENGTH: 22
<212> TYPE: RNA
<213> ORGANISM: Homo sapiens

<400> SEQUENCE: 1
ucguaccgug aguaauaaug cg                                              22

<210> SEQ ID NO 2
<211> LENGTH: 21
<212> TYPE: RNA
<213> ORGANISM: Homo sapiens

<400> SEQUENCE: 2
cauuauuacu uuugguacgc g                                               21

<210> SEQ ID NO 3
<211> LENGTH: 22
```

```
<212> TYPE: RNA
<213> ORGANISM: Homo sapiens

<400> SEQUENCE: 3
uggaguguga caauguguuu ug                                               22

<210> SEQ ID NO 4
<211> LENGTH: 22
<212> TYPE: RNA
<213> ORGANISM: Homo sapiens

<400> SEQUENCE: 4
uuuguucguu cggcucgcgu ga                                               22

<210> SEQ ID NO 5
<211> LENGTH: 22
<212> TYPE: DNA
<213> ORGANISM: Artificial Sequence
<220> FEATURE:
<223> OTHER INFORMATION: miRNA Target

<400> SEQUENCE: 5
cgcattatta ctcacggtac ga                                               22

<210> SEQ ID NO 6
<211> LENGTH: 21
<212> TYPE: DNA
<213> ORGANISM: Artificial Sequence
<220> FEATURE:
<223> OTHER INFORMATION: miRNA target

<400> SEQUENCE: 6
cgcgtaccaa aagtaataat g                                                21

<210> SEQ ID NO 7
<211> LENGTH: 22
<212> TYPE: DNA
<213> ORGANISM: Artificial Sequence
<220> FEATURE:
<223> OTHER INFORMATION: miRNA target

<400> SEQUENCE: 7
caaacaccat tgtcacactc ca                                               22

<210> SEQ ID NO 8
<211> LENGTH: 22
<212> TYPE: DNA
<213> ORGANISM: Artificial Sequence
<220> FEATURE:
<223> OTHER INFORMATION: miRNA target

<400> SEQUENCE: 8
tcacgcgagc cgaacgaaca aa                                               22

<210> SEQ ID NO 9
<211> LENGTH: 65
<212> TYPE: DNA
<213> ORGANISM: Artificial Sequence
<220> FEATURE:
<223> OTHER INFORMATION: 5'UTR

<400> SEQUENCE: 9
gguuccuuaa ucgcggaucc cgcauuauua cucacgguac gaagaucaca ccggucgcca      60
ccaug                                                                  65
```

```
<210> SEQ ID NO 10
<211> LENGTH: 64
<212> TYPE: DNA
<213> ORGANISM: Artificial Sequence
<220> FEATURE:
<223> OTHER INFORMATION: 5'UTR

<400> SEQUENCE: 10
gguuccuuaa ucgcggaucc cgcguaccaa aaguaauaau gagaucacac cggucgccac    60
caug                                                                64

<210> SEQ ID NO 11
<211> LENGTH: 65
<212> TYPE: DNA
<213> ORGANISM: Artificial Sequence
<220> FEATURE:
<223> OTHER INFORMATION: 5'UTR

<400> SEQUENCE: 11
gguuccuuaa ucgcggaucc caaacaccau ugucacacuc caagaucaca ccgucgcca     60 ccaug                                                               65

<210> SEQ ID NO 12
<211> LENGTH: 65
<212> TYPE: DNA
<213> ORGANISM: Artificial Sequence
<220> FEATURE:
<223> OTHER INFORMATION: 5'UTR

<400> SEQUENCE: 12
gguuccuuaa ucgcggaucc ucacgcgagc cgaacgaaca aaagaucaca ccgucgcca     60 ccaug                                                               65

<210> SEQ ID NO 13
<211> LENGTH: 539
<212> TYPE: DNA
<213> ORGANISM: Artificial Sequence
<220> FEATURE:
<223> OTHER INFORMATION: 3'UTR

<400> SEQUENCE: 13
ccugugaugc agaagaaaac acucggcugg gaggccuuca ccgagacgcu guaccccgcu    60
gacggcggcc uggaaggcag aaacgacaug gcccugaagc ucgugggcgg gagccaucug   120
aucgcaaaca ucaagaccac auauagaucc aagaaacccg cuaagaaccu caagaugccu   180
ggcgucuacu auguggacua cagacuggaa agaaucaagg aggccaacaa cgagaccuac   240
gucgagcagc acgagguggc aguggccaga uacugcgacc ucccuagcaa acuggggcac   300
agaucucaua ugcaucucga gugauagucu agaccuucug cggggcuugc cuucuggcca   360
ugcccuucuu cucuccccuug caccuguacc ucuuggucuu ugaauaaagc cugaguagga   420 aaaaaaaaa aaaaaaaaa aaaaaaaaa aaaaaaaaa aaaaaaaaa aaaaaaaaa         480 aaaaaaaaa aaaaaaaaa aaaaaaaaa aaaaaaaaa aaaaaaaaa aaaaaaaa          539

<210> SEQ ID NO 14
<211> LENGTH: 997
<212> TYPE: DNA
<213> ORGANISM: Artificial Sequence
<220> FEATURE:
<223> OTHER INFORMATION: miRNA switch

<400> SEQUENCE: 14
```

```
gguuccuuaa ucgcggaucc cgcauuauua cucacgguac gaagaucaca ccggucgcca        60
ccaugggauc cagcgagcug auuaaggaga acaugcacau gaagcuguac auggagggca       120
ccguggacaa ccaucacuuc aagugcacau ccgagggcga aggcaagccc uacgagggca       180
cccagaccau gagaaucaag guggucgagg gcggcccucu ccccuucgcc uucgacaucc       240
uggcuacuag cuuccucuac ggcagcaaga ccuucaucaa ccacacccag ggcauccccg       300
acuucuucaa gcaguccuuc ccugagggcu ucacauggga gagaguccacc acauacgaag       360 acggggggcgu gcugaccgcu acccaggaca ccagccucca ggacggcugc cucaucuaca       420
acgucaagau cagaggggug aacuucacau ccaacggccc ugugaugcag aagaaaacac       480
ucggcuggga ggccuucacc gagacgcugu accccgcuga cggcggccug aaggcagaa        540 acgacauggc ccugaagcuc gugggcggga gccaucugau cgcaaacauc aagaccacau       600
auagauccaa gaaacccgcu aagaaccuca agaugccugg cgucuacuau guggacuaca       660
gacuggaaag aaucaaggag ccaacaacg agaccuacgu cgagcagcac gagguggcag       720
uggccagaua cugcgaccuc ccuagcaaac uggggcacag aucucauaug caucucgagu       780
gauagucuag accuucugcg ggcuugccu ucuggccaug cccuucuucu cucccuugca       840
ccuguaccuc uuggucuuug aauaaagccu gaguaggaaa aaaaaaaaa aaaaaaaaa       900 aaaaaaaaa aaaaaaaaa aaaaaaaaa aaaaaaaaa aaaaaaaaa aaaaaaaaa          960 aaaaaaaaa aaaaaaaaa aaaaaaaaa aaaaaa                                   997

<210> SEQ ID NO 15
<211> LENGTH: 996
<212> TYPE: DNA
<213> ORGANISM: Artificial Sequence
<220> FEATURE:
<223> OTHER INFORMATION: miRNA switch

<400> SEQUENCE: 15
gguuccuuaa ucgcggaucc cgcguaccaa aaguaauaau gagaucacac cggucgccac        60
caugggaucc agcgagcuga uuaaggagaa caugcacaug aagcuguaca uggagggcac       120
cguggacaac caucacuuca agugcacauc cgagggcgaa ggcaagcccu acgagggcac       180
ccagaccaug agaaucaagg uggucgaggg cggcccucuc cccuucgccu ucgacauccu       240
ggcuacuagc uuccucuacg gcagcaagac cuucaucaac cacacccagg gcauccccga       300
cuucuucaag caguccuucc cugagggcuu cacaugggag agaguccaca cauacgaaga       360
cgggggcgug cugaccgcua cccaggacac cagccuccag gacggcugcc ucaucuacaa       420
cgucaagauc aggggguga acuucacauc caacggcccu gugaugcaga agaaaacacu       480
cggcugggag gccuucaccg agacgcugua ccccgcugac ggcggccugg aaggcagaaa       540
cgacauggcc cugaagcucg ugggcgggag ccaucugauc gcaaacauca agaccacaua       600
uagauccaag aaacccgcua agaaccucaa gaugccuggc gucuacuaug gacuacag         660 acuggaaaga aucaaggagg ccaacaacga gaccuacguc gagcagcacg agguggcagu       720
ggccagauac ugcgaccucc cuagcaaacu ggggcacaga ucucauaugc aucucgagug       780
auagucuaga ccuucugcgg ggcuugccuu cuggccaugc ccuucuucuc ucccuugcac       840
cuguaccucu uggucuuuga auaaagccug aguaggaaaa aaaaaaaaa aaaaaaaaa       900 aaaaaaaaa aaaaaaaaa aaaaaaaaa aaaaaaaaa aaaaaaaaa aaaaaaaaa          960 aaaaaaaaa aaaaaaaaa aaaaaaaaa aaaaaa                                   996
```

<210> SEQ ID NO 16
<211> LENGTH: 997
<212> TYPE: DNA
<213> ORGANISM: Artificial Sequence
<220> FEATURE:
<223> OTHER INFORMATION: miRNA switch

<400> SEQUENCE: 16

| | | | | | |
|---|---|---|---|---|---|
| gguuccuuaa | ucgcggaucc | caaacaccau | ugucacacuc | caagaucaca | ccggucgcca | 60 |
| ccaugggauc | cagcgagcug | auuaaggaga | acaugcacau | gaagcuguac | auggagggca | 120 |
| ccguggacaa | ccaucacuuc | aagugcacau | ccgagggcga | aggcaagccc | uacgagggca | 180 |
| cccagaccau | gagaaucaag | guggucgagg | gcggcccucu | ccccuucgcc | uucgacaucc | 240 |
| uggcuacuag | cuuccucuac | ggcagcaaga | ccuucaucaa | ccacacccag | ggcauccccg | 300 |
| acuucuucaa | gcaguccuuc | ccugagggcu | ucacauggga | gagagucacc | acaucgaag | 360 |
| acggggcgu | gcugaccgcu | acccaggaca | ccagccucca | ggacggcugc | cucaucuaca | 420 |
| acgucaagau | cagaggggug | aacuucacau | ccaacggccc | ugugaugcag | aagaaaacac | 480 |
| ucggcuggga | ggccuucacc | gagacgcugu | accccgcuga | cggcggccug | gaaggcagaa | 540 |
| acgacauggc | ccugaagcuc | gugggcggga | gccaucugau | cgcaaacauc | aagaccacau | 600 |
| auagauccaa | gaaacccgcu | aagaaccuca | agaugccugg | cgucuacuau | guggacuaca | 660 |
| gacuggaaag | aaucaaggag | gccaacaacg | agaccuacgu | cgagcagcac | gagguggcag | 720 |
| uggccagaua | cugcgaccuc | ccuagcaaac | uggggcacag | aucucauaug | caucucgagu | 780 |
| gauagucuag | accuucugcg | gggcuugccu | ucuggcaug | cccuucuucu | cucccuugca | 840 |
| ccuguaccuc | uuggucuuug | aauaaagccu | gaguaggaaa | aaaaaaaaa | aaaaaaaaaa | 900 |
| aaaaaaaaaa | aaaaaaaaaa | aaaaaaaaaa | aaaaaaaaaa | aaaaaaaaaa | aaaaaaaaaa | 960 |
| aaaaaaaaaa | aaaaaaaaaa | aaaaaaaaaa | aaaaaaa | | | 997 |

<210> SEQ ID NO 17
<211> LENGTH: 997
<212> TYPE: DNA
<213> ORGANISM: Artificial Sequence
<220> FEATURE:
<223> OTHER INFORMATION: miRNA switch

<400> SEQUENCE: 17

| | | | | | |
|---|---|---|---|---|---|
| gguuccuuaa | ucgcggaucc | ucacgcgagc | cgaacgaaca | aaagaucaca | ccggucgcca | 60 |
| ccaugggauc | cagcgagcug | auuaaggaga | acaugcacau | gaagcuguac | auggagggca | 120 |
| ccguggacaa | ccaucacuuc | aagugcacau | ccgagggcga | aggcaagccc | uacgagggca | 180 |
| cccagaccau | gagaaucaag | guggucgagg | gcggcccucu | ccccuucgcc | uucgacaucc | 240 |
| uggcuacuag | cuuccucuac | ggcagcaaga | ccuucaucaa | ccacacccag | ggcauccccg | 300 |
| acuucuucaa | gcaguccuuc | ccugagggcu | ucacauggga | gagagucacc | acaucgaag | 360 |
| acggggcgu | gcugaccgcu | acccaggaca | ccagccucca | ggacggcugc | cucaucuaca | 420 |
| acgucaagau | cagaggggug | aacuucacau | ccaacggccc | ugugaugcag | aagaaaacac | 480 |
| ucggcuggga | ggccuucacc | gagacgcugu | accccgcuga | cggcggccug | gaaggcagaa | 540 |
| acgacauggc | ccugaagcuc | gugggcggga | gccaucugau | cgcaaacauc | aagaccacau | 600 |
| auagauccaa | gaaacccgcu | aagaaccuca | agaugccugg | cgucuacuau | guggacuaca | 660 |
| gacuggaaag | aaucaaggag | gccaacaacg | agaccuacgu | cgagcagcac | gagguggcag | 720 |
| uggccagaua | cugcgaccuc | ccuagcaaac | uggggcacag | aucucauaug | caucucgagu | 780 |

```
gauagucuag accuucugcg gggcuugccu ucuggccaug cccucuucu cucccuugca    840 ccuguaccuc uuggucuuug aauaaagccu gaguaggaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaa                             997

<210> SEQ ID NO 18
<211> LENGTH: 992
<212> TYPE: DNA
<213> ORGANISM: Artificial Sequence
<220> FEATURE:
<223> OTHER INFORMATION: tagBFP

<400> SEQUENCE: 18
gggcgaauua agagagaaaa gaagaguaag aagaaauaua agacaccggu cgccaccaug    60
ggauccagcg agcugauuaa ggagaacaug cacaugaagc uguacaugga gggcaccgug   120
gacaaccauc acuucaagug cacauccgag ggcgaaggca agcccuacga gggcacccag   180
accaugagaa ucaaggguggu cgagggcggc ccucuccccu cgccuucga cauccuggcu   240 acuagcuucc ucuacggcag caagaccuuc aucaaccaca cccagggcau ccccgacuuc   300
uucaagcagu ccuucccuga gggcuucaca ugggagagag ucaccacaua cgaagacggg   360
ggcgugcuga ccgcuaccca ggacaccagc uccaggacg gcugccucau cuacaacguc   420
aagaucagag ggugaacuu cacauccaac ggcccuguga ugcagaagaa acacucggc    480 ugggaggccu ucaccgagac gcuguacccc gcugacggcg gccuggaagg cagaaacgac   540
auggcccuga agcucgugg gggagccau cugaucgcaa acaucaagac cacauauaga    600
uccaagaaac ccgcuaagaa ccucaagaug ccuggcgucu acauguggga cuacagacug   660
gaaagaauca aggaggccaa caacgagacc uacgucgagc agcacgaggu ggcaguggcc   720
agauacugcg accuccuag caaacugggg cacagaucuc auaugcaucu cgagugauag   780
ucuagaccuu cugcggggcu ugccuucugg ccaugcccuu cuucucucc uugcaccugu   840 accucuuggu cuuugaauaa agccugagua ggaaaaaaaa aaaaaaaaaa aaaaaaaaaa   900
aaaaaaaaaa aaaaaaaaaa aaaaaaaaaa aaaaaaaaaa aaaaaaaaaa aaaaaaaaaa   960
aaaaaaaaaa aaaaaaaaaa aaaaaaaaaa aa                                 992

<210> SEQ ID NO 19
<211> LENGTH: 1019
<212> TYPE: DNA
<213> ORGANISM: Artificial Sequence
<220> FEATURE:
<223> OTHER INFORMATION: EGFP

<400> SEQUENCE: 19
gggcgaauua agagagaaaa gaagaguaag aagaaauaua agacaccggu cgccaccaug    60
ggauccguga gcaagggcga ggagcuguuc accggggugg ugcccauccu ggucgagcug   120
gacggcgacg uaaacggcca caaguucagc gugucaggcg agggcgaggg cgaugccacc   180
uacggcaagc ugacccugaa guucaucugc accaccggca agcugcccgu gcccuggccc   240
acccucguga ccaccugac cuacggcgug cagugcuuca gccgcuaccc cgaccacaug   300
aagcagcacg acuucuucaa guccgccaug cccgaaggcu acguccagga gcgcaccauc   360
uucuucaagg acgacggcaa cuacaagacc cgcgccgagg ugaaguucga gggcgacacc   420 cugguggaaacc gcaucgagcu gaagggcauc gacuucaagg aggacggcaa cauccugggg   480
```

| | |
|---|---|
| cacaagcugg aguacaacua caacagccac aacgucuaua ucauggccga caagcagaag | 540 |
| aacggcauca aggugaacuu caagauccgc cacaacaucg aggacggcag cgugcagcuc | 600 |
| gccgaccacu accagcagaa cacccccauc ggcgacggcc ccgugcugcu gcccgacaac | 660 |
| cacuaccuga gcacccaguc cgcccugagc aaagacccca acgagaagcg cgaucacaug | 720 |
| guccugcugg aguucgugac cgccgccggg aucacucucg caug gacga gcuguacaag | 780 |
| agaucucaua ugcaucucga gugauagucu agaccuucug cggggcuugc cuucuggcca | 840 |
| ugcccuucuu cucucccuug caccuguacc ucuuggucuu ugaauaaagc cugaguagga | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaaaa | 1019 |

<210> SEQ ID NO 20
<211> LENGTH: 668
<212> TYPE: DNA
<213> ORGANISM: Artificial Sequence
<220> FEATURE:
<223> OTHER INFORMATION: Blastcidin

<400> SEQUENCE: 20

| | |
|---|---|
| gggcgaauua agagagaaaa gaagaguaag aagaaauaua agacaccggu cgccaccaug | 60 |
| gccaagccuu ugucucaaga agaauccacc cucauugaaa gagcaacggc uacaaucaac | 120 |
| agcaucccca ucucugaaga cuacagcguc gccagcgcag cucucucuag cgacggccgc | 180 |
| aucuucacug gugucaaugu auaucauuuu acuggggga c cuugugcaga acucguggug | 240 |
| cugggcacug cugcugcugc ggcagcuggc aaccugacuu guaucgucgc gaucggaaau | 300 |
| gagaacaggg gcaucuugag ccccugcgga cggugccgac aggugcuucu cgaucugcau | 360 |
| ccugggauca aagccauagu gaaggacagu gauggacagc cgacggcagu ggga uucgu | 420 |
| gaauugcugc ccucugguua uguguggag ggcuaaucua gaccuucugc ggggcuugcc | 480 |
| uucuggccau gcccuucuuc ucucccuugc accuguaccu cuuggucuuu gaauaaagcc | 540 |
| ugaguaggaa aaaaaaaaaa aaaaaaaaaa aaaaaaaaaa aaaaaaaaaa aaaaaaaaaa | 600 |
| aaaaaaaaaa aaaaaaaaaa aaaaaaaaaa aaaaaaaaaa aaaaaaaaaa aaaaaaaaaa | 660 |
| aaaaaaaa | 668 |

<210> SEQ ID NO 21
<211> LENGTH: 869
<212> TYPE: DNA
<213> ORGANISM: Artificial Sequence
<220> FEATURE:
<223> OTHER INFORMATION: Puromycin resistance

<400> SEQUENCE: 21

| | |
|---|---|
| gggcgaauua agagagaaaa gaagaguaag aagaaauaua agacaccggu cgccaccaug | 60 |
| accgaguaca gcccacggu gcgccucgcc cccgcgacg acguccccg ggccgua cgc | 120 |
| acccucgccg ccgcguucgc cgacuacccc gccacgcgcc acaccgucga uccgaccgc | 180 |
| cacaucgagc ggg ucaccga gcugcaagaa cucuuccuca cgcgcgucgg cucgacauc | 240 |
| ggcaaggugu gggucgcgga cgacggcgcc gcgguggcgg ucuggaccac gccgagagc | 300 |
| gucgaagcgg gggcggugu u cgccgagauc ggcccgcgca uggccgaguu gagcgguucc | 360 |
| cggcuggccg cgcagcaaca gaugga aggc cuccuggcgc cgcaccggcc caaggagccc | 420 |
| gcgugguucc uggccaccgu cggcgucucg cccgaccacc agggcaaggg ucugggcagc | 480 |
| gccgucgugc uccccggagu ggaggcggcc gagcgcgccg gggugcccgc cuuccuggag | 540 |

```
accuccgcgc cccgcaaccu ccccuucuac gagcggcucg gcuucaccgu caccgccgac    600
gucgaggugc ccgaaggacc gcgcaccugg ugcaugaccc gcaagcccgg ugccugaucu    660
agaccuucug cggggcuugc cuucuggcca ugcccuucuu cucucccuug caccuguacc    720
ucuuggucuu ugaauaaagc cugaguagga aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaa                                     869
```